(12) United States Patent
Ishiwata

(10) Patent No.: US 9,594,941 B2
(45) Date of Patent: *Mar. 14, 2017

(54) PHASE DISTRIBUTION MEASUREMENT METHOD AND PHASE DISTRIBUTION MEASUREMENT APPARATUS

(71) Applicant: OLYMPUS CORPORATION, Shibuya-ku, Tokyo (JP)

(72) Inventor: Hiroshi Ishiwata, Tokyo (JP)

(73) Assignee: OLYMPUS CORPORATION, Tokyo (JP)

(*) Notice: Subject to any disclaimer, the term of this patent is extended or adjusted under 35 U.S.C. 154(b) by 192 days.

This patent is subject to a terminal disclaimer.

(21) Appl. No.: 14/189,532

(22) Filed: Feb. 25, 2014

(65) Prior Publication Data

US 2014/0285650 A1 Sep. 25, 2014

(30) Foreign Application Priority Data

Mar. 22, 2013 (JP) ................. 2013-059327
Nov. 25, 2013 (JP) ................. 2013-242448

(51) Int. Cl.
*G06K 9/00* (2006.01)
*G01N 15/14* (2006.01)
(Continued)

(52) U.S. Cl.
CPC ..... *G06K 9/00127* (2013.01); *G01N 15/1475* (2013.01); *G02B 21/0056* (2013.01);
(Continued)

(58) Field of Classification Search
CPC ............ G06K 9/00127; G06K 9/0014; G01N 15/1475; G01N 21/41; G02B 21/0056;
(Continued)

(56) References Cited

U.S. PATENT DOCUMENTS 5,239,364 A * 8/1993 Matsuzaki ............... G01J 9/02
356/515
5,420,717 A * 5/1995 Tabata .................. G02B 5/3083
359/371
(Continued)

FOREIGN PATENT DOCUMENTS

JP  7-225341 A   8/1995
JP  09-015504 A  1/1997
(Continued)

OTHER PUBLICATIONS

Non-Final Office Action dated Aug. 23, 2016, issued in U.S. Appl. No. 14/571,244.
(Continued)

*Primary Examiner* — Gelek W Topgyal
(74) *Attorney, Agent, or Firm* — Holtz, Holtz & Volek PC

(57) ABSTRACT

A phase distribution measurement method inside a biological sample includes taking in an optical image of the sample formed by a microscope to form a plurality of images with different image contrasts; calculating a component corresponding to phase distribution of the sample and a component corresponding to other than the phase distribution, and dividing the component corresponding to the phase distribution by the component corresponding to other than the phase distribution to form a normalized phase component image; breaking down the phase component image into a plurality of frequency components; performing a deconvolution process to each of the frequency components using an optical response character corresponding to each, and calculating phase distribution of a refraction component and phase distribution of a structure component; and calculating phase distribution of the sample by compounding the phase distribution of the refraction component and the phase distribution of the structure component.

20 Claims, 18 Drawing Sheets

(51) Int. Cl.
G02B 21/00 (2006.01)
G02B 21/14 (2006.01)
G02B 21/16 (2006.01)
G02B 21/36 (2006.01)

(52) U.S. Cl.
CPC ......... *G02B 21/0068* (2013.01); *G02B 21/14* (2013.01); *G02B 21/16* (2013.01); *G02B 21/365* (2013.01); *G06K 9/0014* (2013.01)

(58) Field of Classification Search
CPC  G02B 21/0068; G02B 21/365; G06T 7/0012; A61B 5/1455
USPC ... 250/458.1, 208.2, 214.1, 216, 221, 358.1; 348/79–80; 359/368–386
See application file for complete search history.

(56) References Cited

U.S. PATENT DOCUMENTS

| | | | |
|---|---|---|---|
| 5,751,475 A | 5/1998 | Ishiwata et al. | |
| 6,025,956 A | 2/2000 | Nagano et al. | |
| 6,674,574 B1* | 1/2004 | Aono | G02B 21/025 250/201.3 |
| 6,741,356 B1* | 5/2004 | Ishiwata | G01B 9/04 356/491 |
| 7,233,434 B2 | 6/2007 | Shribak | |
| 7,564,618 B2 | 7/2009 | Shribak | |
| 8,446,668 B2* | 5/2013 | Matsui | G02B 21/14 359/368 |
| 8,809,809 B1* | 8/2014 | Wu | G02B 21/16 250/458.1 |
| 2002/0167724 A1* | 11/2002 | Iketaki | G02B 21/06 359/385 |
| 2003/0132394 A1* | 7/2003 | Wolleschensky | G01N 21/6458 250/458.1 |
| 2008/0032325 A1* | 2/2008 | DiMarzio | G02B 21/0004 435/29 |
| 2009/0225407 A1* | 9/2009 | Nakayama | G02B 21/16 359/370 |
| 2009/0306487 A1* | 12/2009 | Crowe | A61B 5/02433 600/322 |
| 2012/0057013 A1 | 3/2012 | Ishiwata | |
| 2014/0118721 A1* | 5/2014 | Shyu | G03F 7/70633 356/51 |
| 2015/0185460 A1 | 7/2015 | Nakasho et al. | |

FOREIGN PATENT DOCUMENTS

| | | |
|---|---|---|
| JP | 09179034 A | 7/1997 |
| JP | 2006-300714 A | 11/2006 |
| JP | 2007-140572 A | 6/2007 |
| JP | 2008-102294 A | 5/2008 |
| JP | 2008-111726 A | 5/2008 |
| JP | 2012-73591 A | 4/2012 |

OTHER PUBLICATIONS

Axelrod, et al., "Topographic profiling and refractive-index analysis by use of differential interference contrast with bright-field intensity and atomic force imaging", Applied Optics vol. 43, No. 11 (Apr. 2004), pp. 2272-2284.
Bon, et al., "Optical detection and measurement of living cell morphometric features with single-shot quantitative phase microscopy", Journal of Biomedical Optics vol. 17, No. 7 (Jul. 2012), pp. 076004-1-076004-7.
Shribak, "Quantitative orientation-independent differential interference contrast microscope with fast switching shear direction and bias modulation", Journal of the Optical Society of America, vol. 30, No. 4 (Apr. 2013), pp. 769-782.
Van Munster, et al., "Reconstruction of optical pathlength distributions from images obtained by a wide-field differential interference contrasts microscope", Journal of Microscopy vol. 188, No. 2 (Nov. 1997), pp. 149-157.
Related U.S. Appl. No. 14/571,244; First Named Inventor: Eiji Nakasho; Title: "Image Forming Method and Image Forming Apparatus"; Filed: Feb. 25, 2014.
U.S. Appl. No. 14/571,244; First Named Inventor: Eiji Nakasho; Title: "Image Forming Method and Image Forming Apparatus"; filed Dec. 15, 2014.
David A. Agard, et al. "Fluorescence Microscopy in three dimensions" Chapter 3, Methods in Cell Biology, vol. 30 (1989), pp. 353-377 (in English).
Michael Shribak, et al. "Orientation-independent differential interference contrast microscopy and its combination with an orientation-independent polarization system", Journal of Biomedical Optics 13(1), (Jan./Feb. 2008), pp. 014011-1-014011-10 (in English).
Final Office Action dated Dec. 14, 2016, issued in U.S. Appl. No. 14/571,244.
Mehta, et al., "Sample-less calibration of the differential interference contrast microscope", Applied Optics, vol. 49, No. 15 (May 2010), pp. 2954-2968.

* cited by examiner

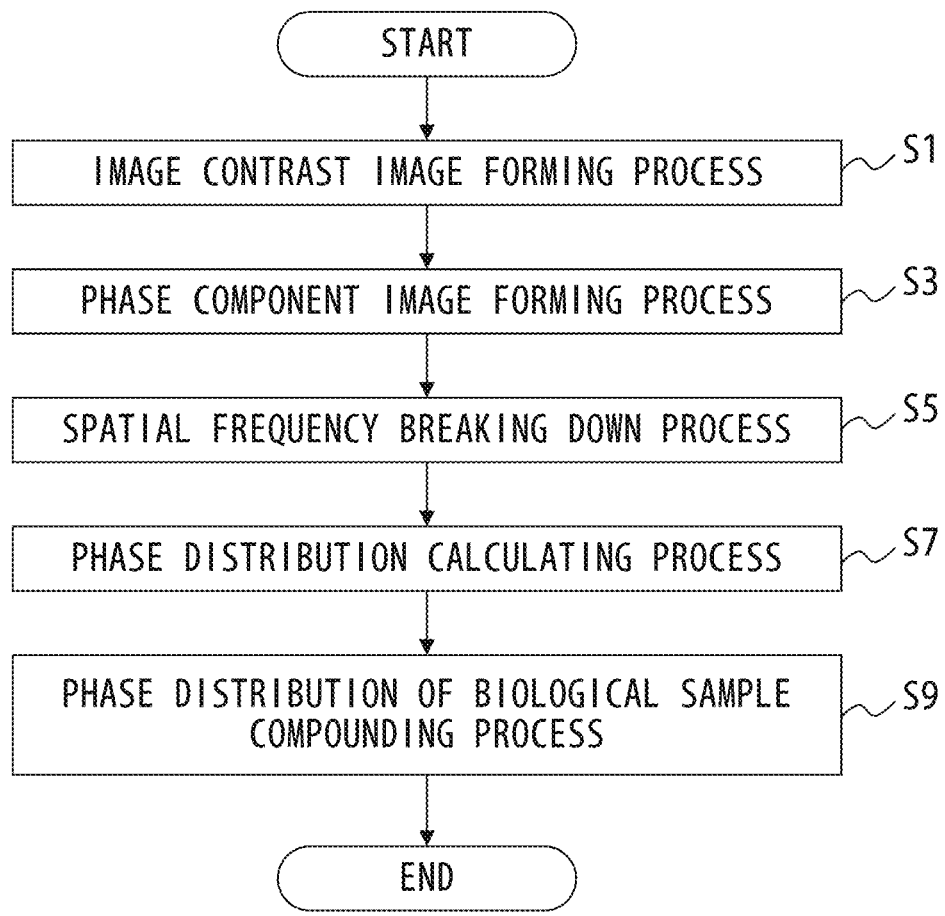
F I G. 1

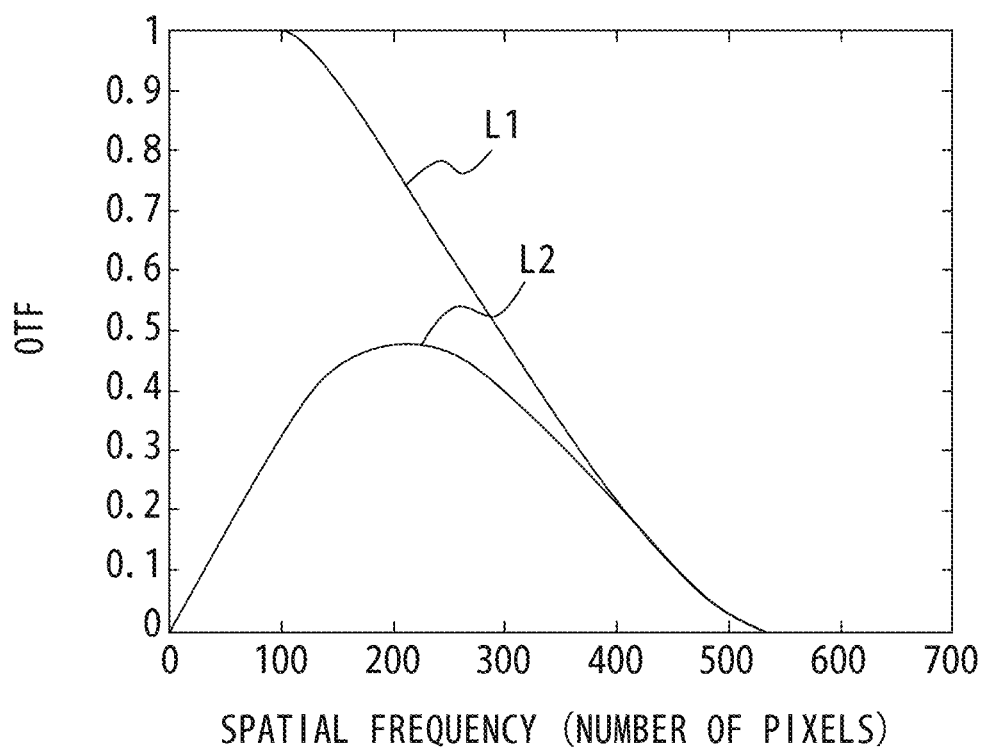
F I G. 3

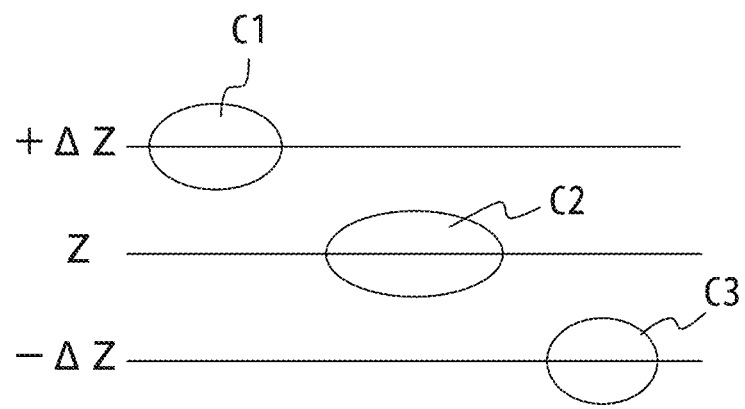
F I G. 4

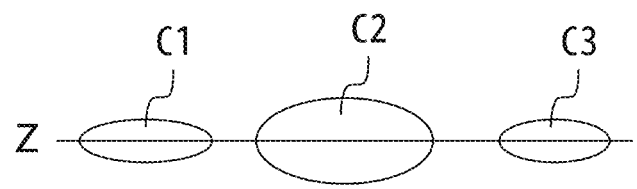
F I G. 5

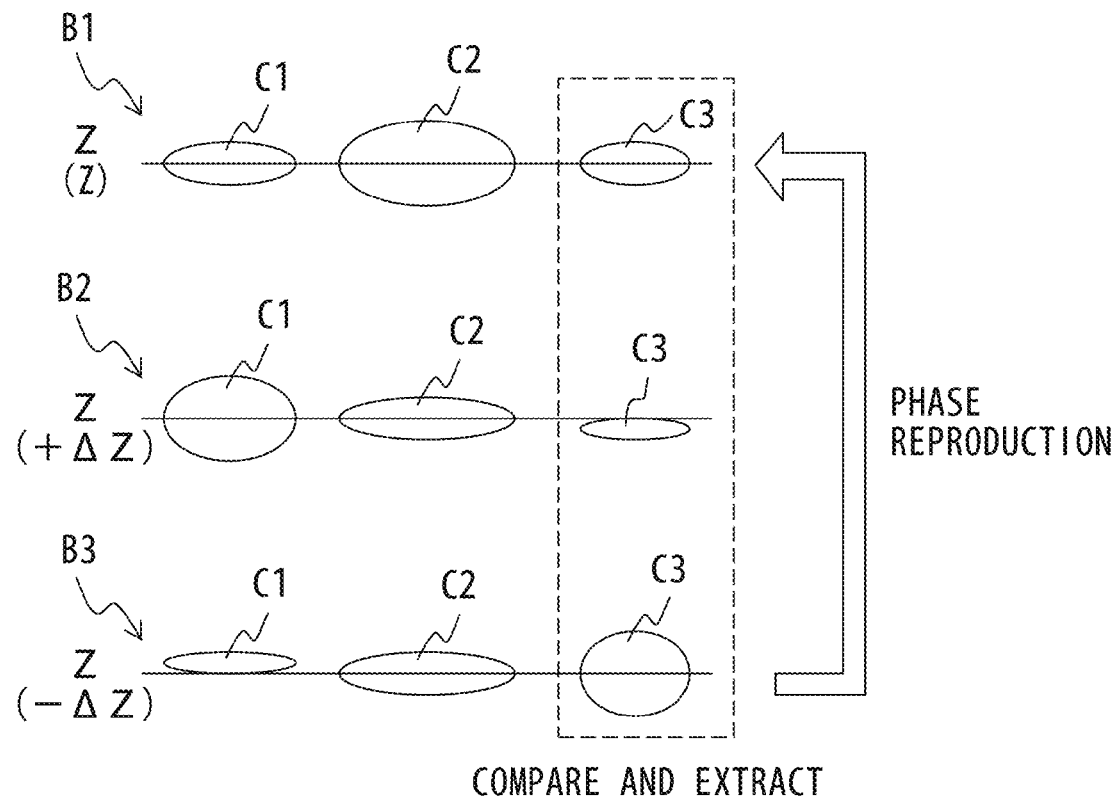
F I G. 6

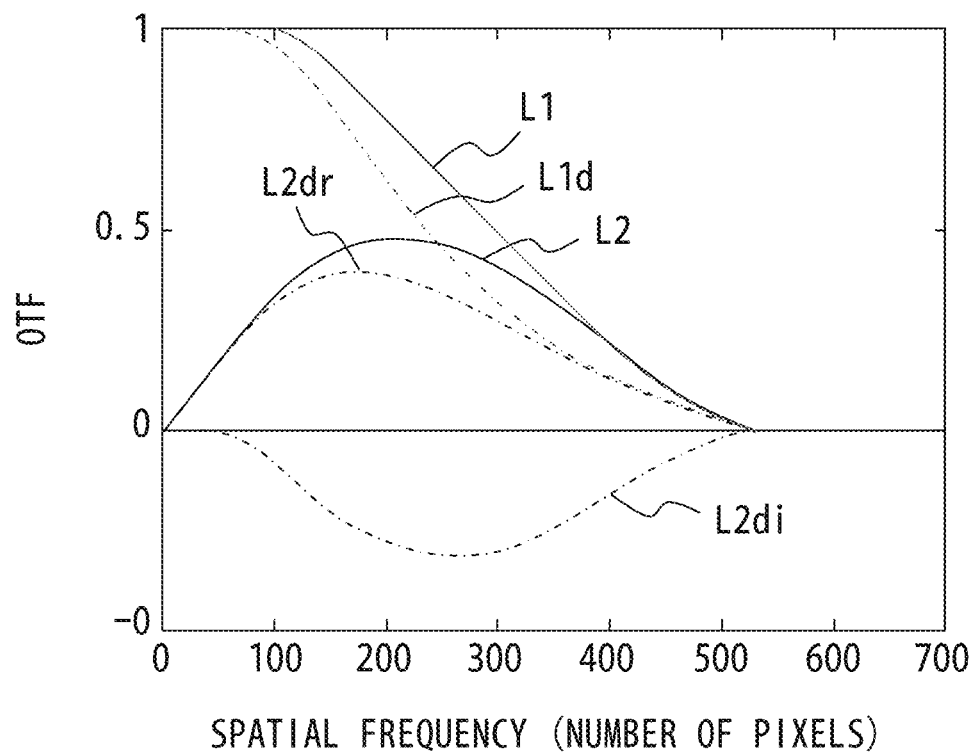
F I G. 7

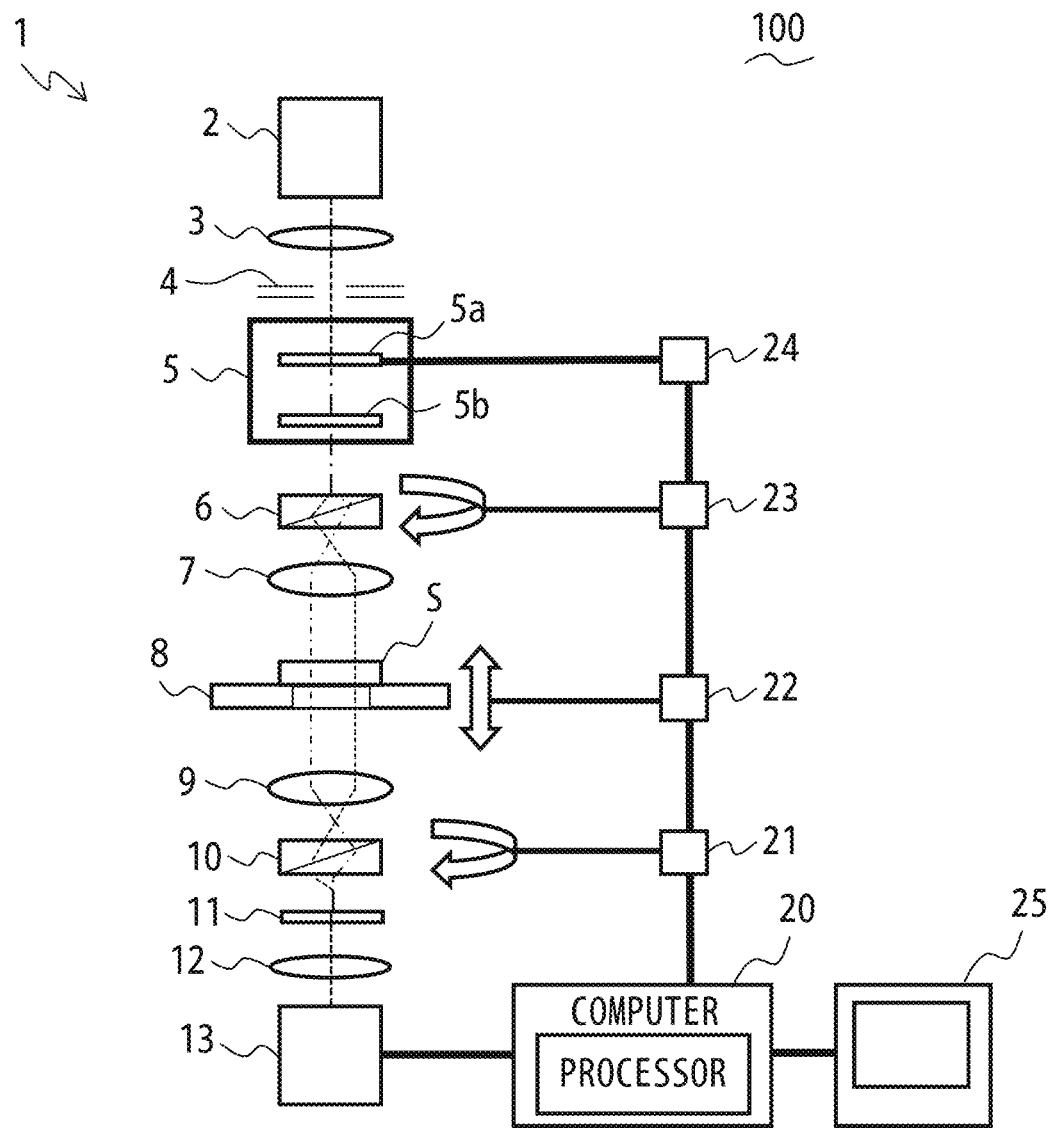
F I G. 10

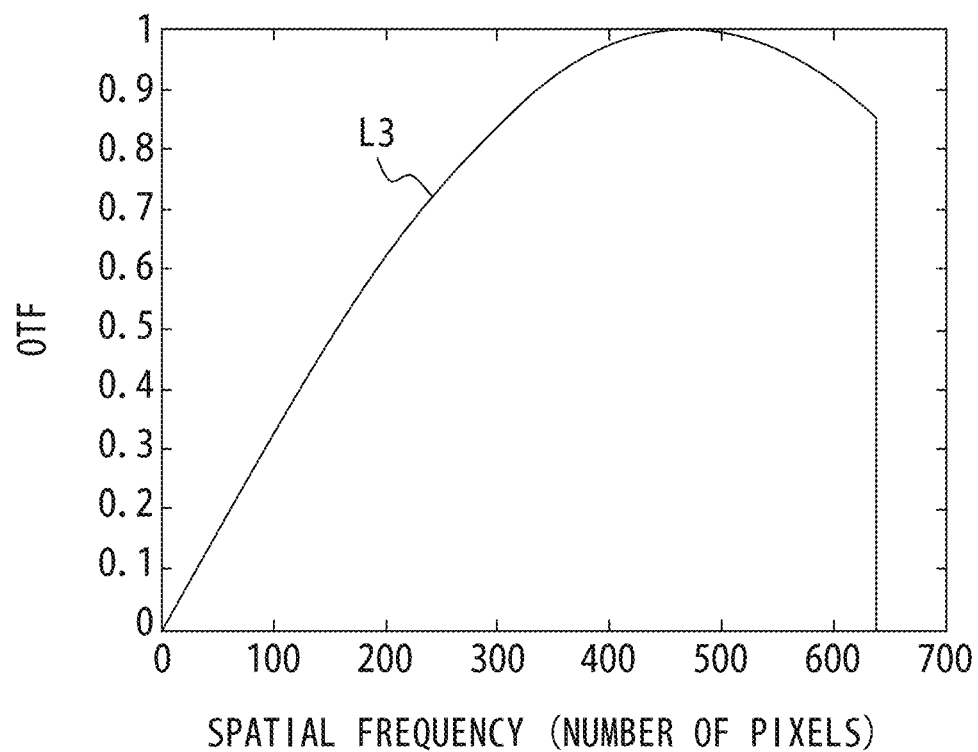
F I G. 11

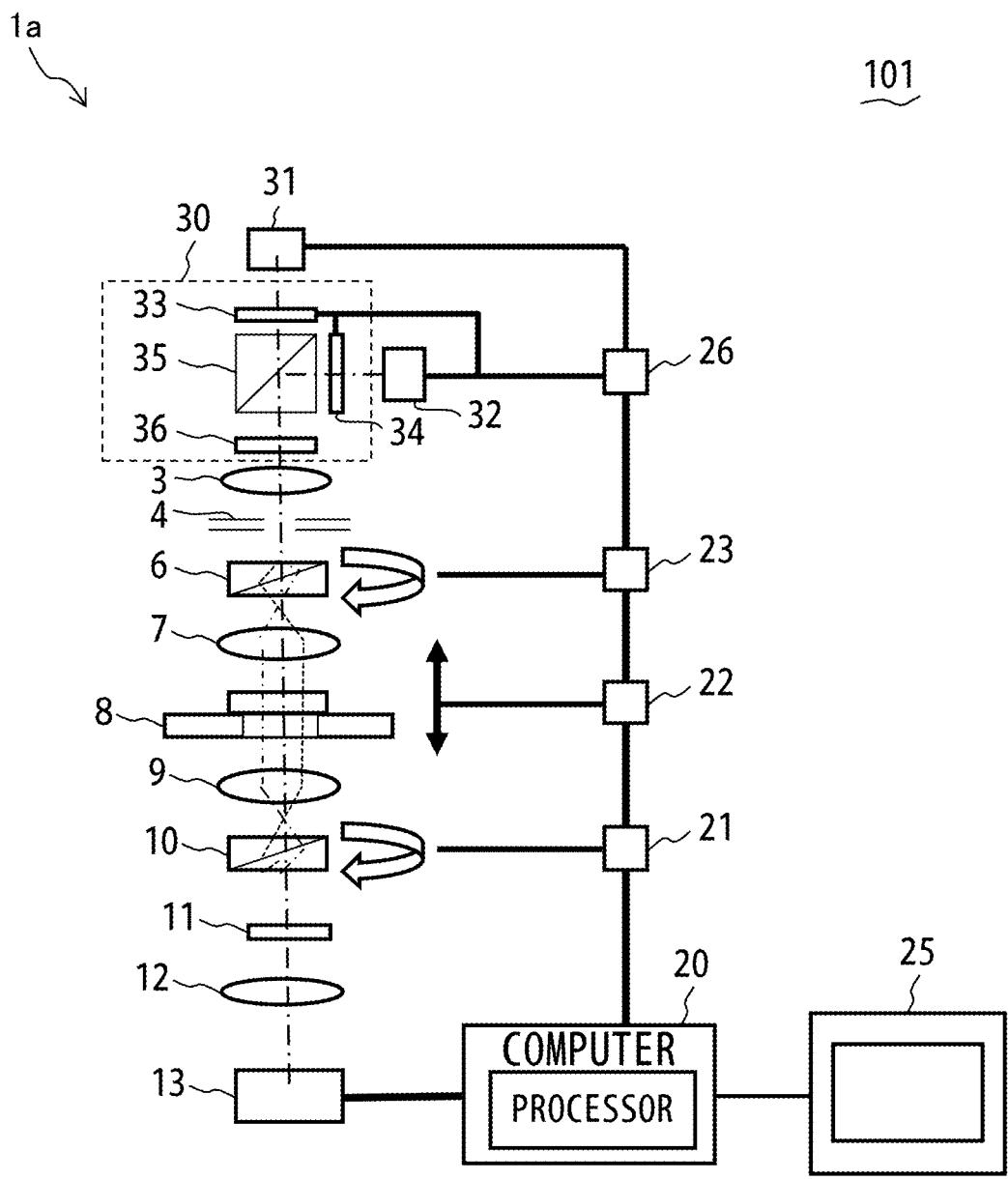
F I G. 1 3

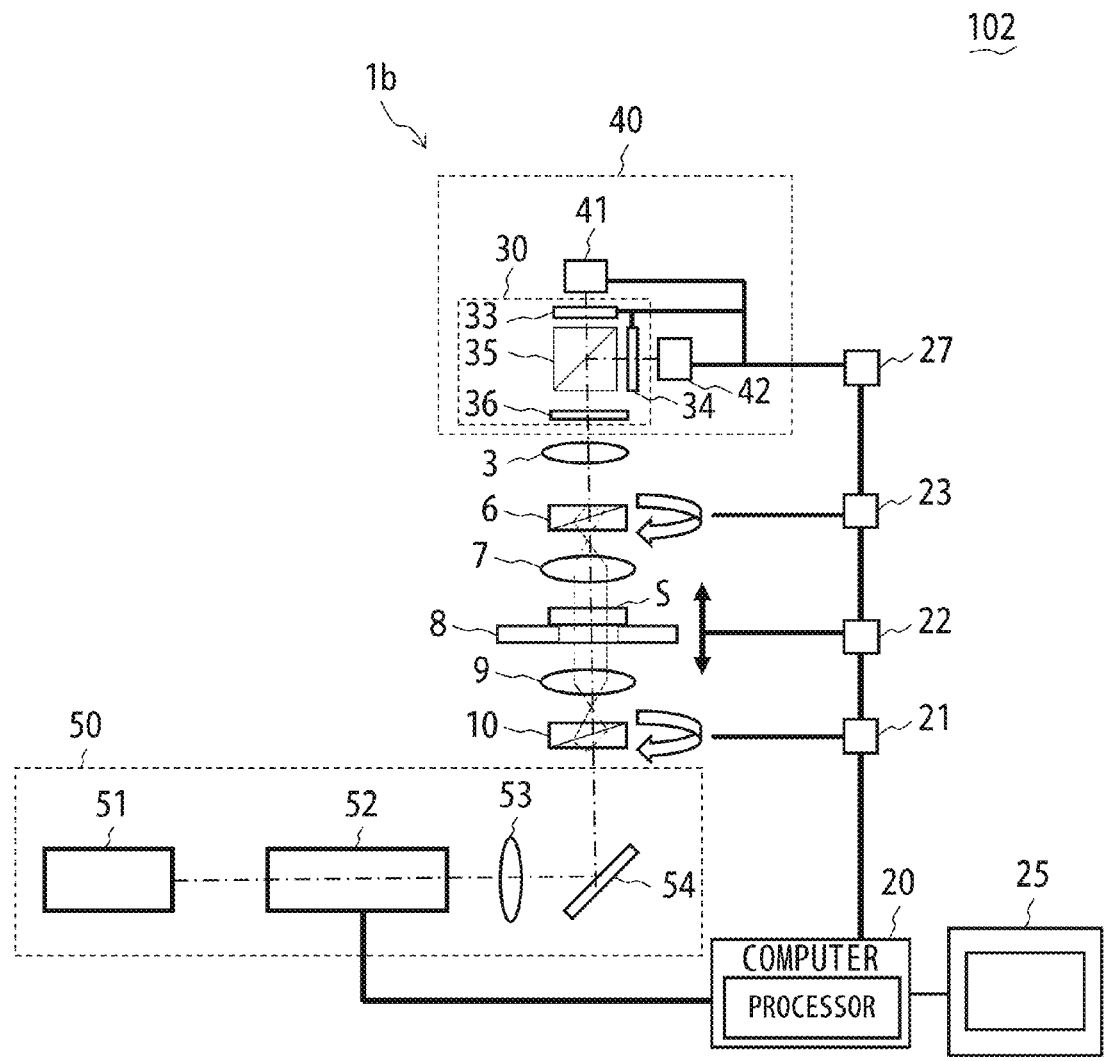
F I G. 15

PHASE DISTRIBUTION MEASUREMENT METHOD AND PHASE DISTRIBUTION MEASUREMENT APPARATUS

CROSS-REFERENCE TO RELATED APPLICATION

This application is based upon and claims the benefit of priority from prior Japanese Patent Applications Nos. 2013-059327 filed on Mar. 22, 2013 and 2013-242448 filed on Nov. 25, 2013, the entire contents of which are incorporated herein by these references.

FIELD

The present invention relates to a method and an apparatus for obtaining the phase distribution of a phase object such as a living cell and a living tissue.

BACKGROUND

As methods to observe a transparent and colorless living cell and living tissue, a method to observe the living cell in a state as it is using a phase contrast microscope, a differential interference contrast microscope and the like, a method to form and dye a thin strip samples from a living tissue and observe them with a bright field microscope, a method to observe a thin strip sample using a phase contrast microscope, a differential interference contrast microscope and the like without dyeing have been known. Meanwhile, a method to observe a living tissue and the like using a differential interference contrast microscope is disclosed in Japanese Laid-open Patent Publication No. 09-015504 and the like.

Other than these, a method to observe a living cell and a living tissue with a fluorescence confocal microscope after dyeing them with a fluorochrome, or making the living cell and the living tissue express fluorescent protein such as GFP (Green Fluorescent Protein) by gene transfer has also been known. Since a fluorescence confocal microscope has a good three-dimensional resolution, when observing a living tissue, it is possible to observe the three-dimensional structure without forming any strip sample. For this reason, currently, the fluorescent observing method using a fluorescence confocal microscope is most popular as a method used in observing the fine three-dimensional structure of a living cell and living tissue.

Incidentally, due to the emergence of pluripotent stem cells such as iPS cells (induced pluripotent stem cells) and ES cells (embryonic stem cells) that enables regeneration of tissues of and nerves of organs by induction of differentiation, it is expected that regenerative medicine to cure a number of disorders by transplanting tissues and nerves of organs regenerated with iPS cells and ES cells into the living body becomes possible. Then, studies for its clinical application are under way.

The mutation of iPS cells and ES cells themselves, or, the mutation occurring in tissues and the like regenerated by induction of differentiation of the cells such as tumorigenic transformation is not desirable especially in the clinical application in regenerative medicine and should be avoided. For this reason, in the studies for clinical application, efforts have been made to check mutation and alteration in each process from the cell level to the tissue and organ to be regenerated.

SUMMARY

An aspect of the present invention provides a phase distribution measurement method inside a biological sample includes taking in an optical image of a biological sample formed by a microscope that converts phase distribution into image intensity distribution while changing image contrast to form a plurality of pieces of images with different image contrasts; calculating a component corresponding to phase distribution of the biological sample and a component corresponding to other than the phase distribution of the biological sample, and dividing the component corresponding to the phase distribution by the component corresponding to other than the phase distribution of the biological sample to form a normalized phase distribution image; breaking down the phase component image into a plurality of frequency components based on a spatial frequency of the image; performing a deconvolution process to each of the frequency components using an optical response character corresponding to each, and calculating phase distribution of a refraction component formed by light refracted inside the biological sample and phase distribution of a structure component formed by light diffracted in a structure inside the biological sample; and calculating phase distribution of the biological sample by compounding the phase distribution of the refraction component and the phase distribution of the structure component.

Another aspect of the present invention provides a phase distribution measurement apparatus including a microscope configured to convert phase distribution of a biological sample into image intensity distribution, comprising an image contrast changing unit configured to change image contrast of the image intensity distribution; a control unit configured to control the image contrast changing unit so as to obtain a plurality of pieces of images with different image contrasts; and a calculating unit configured to calculate phase distribution of the biological sample from the plurality of pieces of images obtained by control the control unit performs, according to the phase distribution measurement method described in the aspect mentioned above.

BRIEF DESCRIPTION OF DRAWINGS

The present invention will be more apparent from the following detailed description when the accompanying drawings are referenced.

FIG. 1 is a flowchart of a phase distribution measuring method according to an embodiment of the present invention.

FIG. 3 is a diagram illustrating optical response character corresponding to the structural component in the focused state with respect to the observation plane.

FIG. 4 is a diagram illustrating the three-dimensional structure of a biological sample.

FIG. 5 is a diagram schematically illustrating the phase distribution obtained with optical response character in the focused state.

FIG. 6 is a diagram for illustrating an example of a method to reproduce phase distribution in which blurring occurred due to defocusing.

FIG. 7 is a diagram illustrating optical response character corresponding to the structural component in the defocused state with respect to the observation plane.

FIG. 10 is a diagram illustrating a configuration of a microscope system according to embodiment 1 of the present invention.

FIG. 11 is a diagram illustrating optical response character corresponding to the refraction component in the focused state with respect to the observation plane.

FIG. 13 is a diagram illustrating a configuration of a microscope system according to embodiment 2 of the present invention.

FIG. 15 is a diagram illustrating a configuration of a microscope system according to embodiment 3 of the present invention.

DESCRIPTION OF EMBODIMENTS

Figure 2:
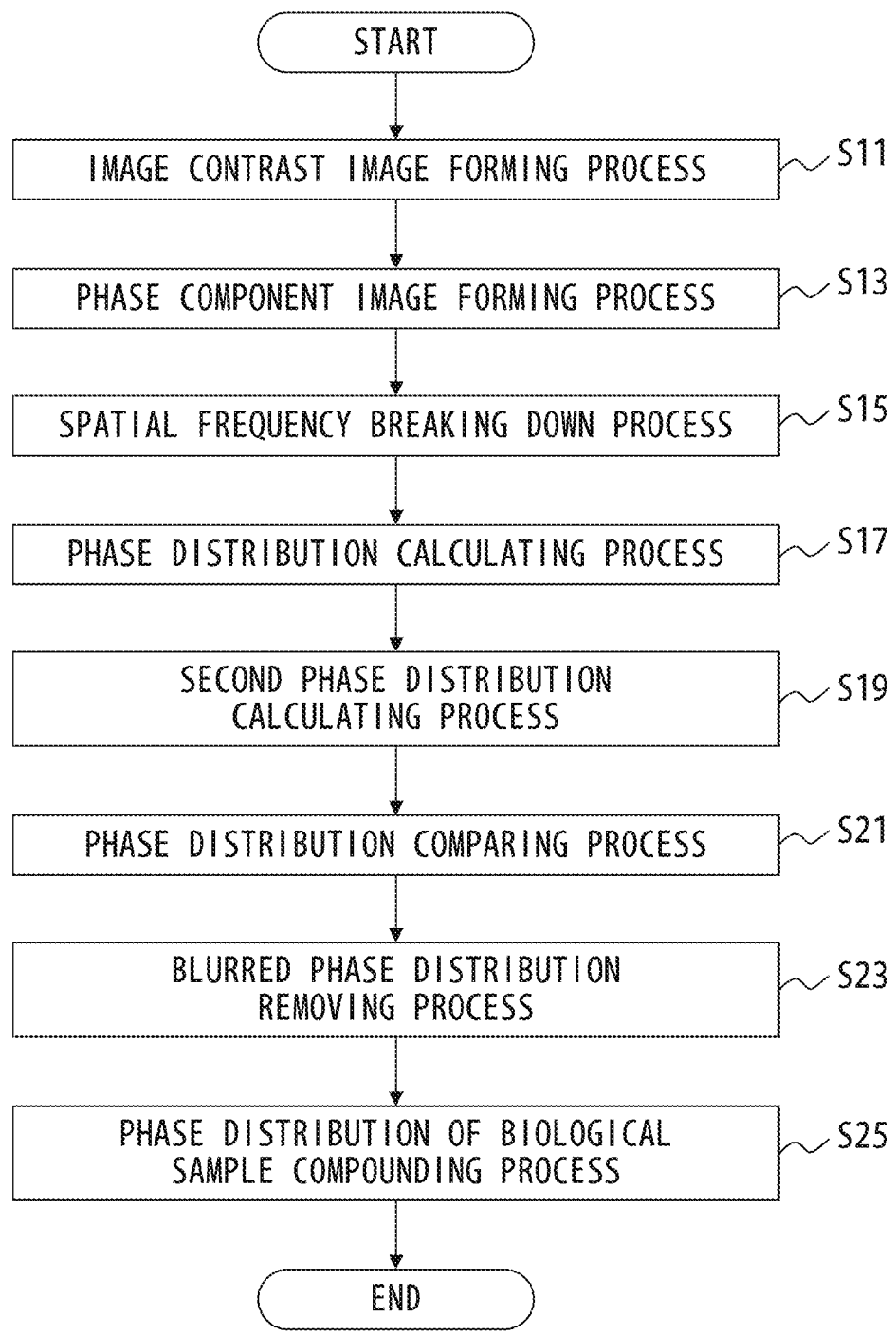
FIG. 2 is another flowchart of a phase distribution measuring method according to an embodiment of the present invention.

The iPS cells and ES cells has a characteristic to form a sterically-stabilized aggregation called a colony as cell division goes on, and even a cultured cell has a three-dimensionally complicated structure in the same manner as the living tissue. For this reason, to check the mutation and alteration of these cells in each process, a technique to observe a three-dimensionally complicated structure.

However, with the method using a fluorescence confocal microscope that is used most popularly to observe the three-dimensional structure of living cells and living tissues currently, the application of a fluorochrome, the expression of fluorescent protein are required for observation. With the transplantation of a regenerated tissue and organ in which the fluorochrome and fluorescent protein is incorporated, there are concerns about the effects on the human body, in the same manner as the tissue's mutation and alteration. For this reason, it is difficult to use this method for the check.

Meanwhile, while observation methods to perform confocal observation using a non-linear optical phenomenon such as SHG (second harmonic generation) generated when the observed object is irradiated with a strong laser light has also been invented, but in these methods, the possibility that the damage to cells and tissues due to the irradiation of the strong laser light causes mutation and alteration is not low. For this reason, this method is not suitable for checking mutation and alteration in each process.

Due to the actual situation described above, in the field of clinical application of regenerative medicine, as a technique with which living cells and living tissues having a three-dimensional structure can be checked without applying any fluorochrome and the like, further improvement in the technique to observe a three-dimensional structure by obtaining phase distribution is desired.

First, living cells and living tissues that are the sample being the subject of the present invention (hereinafter, there are collectively referred to as a biological sample) are explained.

A biological sample having a three-dimensional structure has characteristics that while being transparent and colorless, it changes the phase of the light passing through due to the difference in its internal composition and the like. According to this, a biological sample may be regarded as a phase object having phase distribution that changes continuously in three dimensions. For this reason, when the three-dimensional phase distribution of a biological sample is obtained, it becomes possible to know its three-dimensional structure.

The present invention relates to a technique to detect phase distribution of an observation area having a certain thickness in the optical axis direction in a biological sample (phase object), and the three-dimensional phase distribution of the biological sample is obtained by connecting phase distributions of a plurality of observation areas at different positions in the optical axis direction. This is a totally different technique from the fluorescent confocal microscope that detects the three-dimensional position of a fluorochrome in the observed object and forms a three-dimensional image from the detected positions of fluorochromes.

Next, an overview of the past research results by the inventor of the present invention regarding the measurement of phase distribution of phase objects in general not limited to biological samples and new challenges regarding the measurement of phase distribution of biological samples found by the inventor of the present invention is given.

Japanese Laid-open Patent Publication No. 2008-102294 discloses a characteristic that for a phase object, when bright field observation is performed, no image is generated at the focus position, but image contrast is generated at a position away from the focus. Meanwhile, Japanese Laid-open Patent Publication No. 9-15504 discloses that image intensity distribution of the time when phase object is observed with a differential interference contrast microscope includes, other than image intensity distribution representing differentiation of phase distribution, a plurality of image components.

the inventor of the present invention has found the following (1) and (2). (1) In the plurality of image components presented in Japanese Laid-open Patent Publication No. 9-15504, an image component generated by defocusing presented in Japanese Laid-open Patent Publication No. 2008-102294 is included. (2) When a phase object has a three-dimensional structure, the image component generated by the defocusing (image component due to phase distribution outside the observation area) to the observation is not negligible.

Meanwhile, Japanese Laid-open Patent Publication No. 9-15504 discloses that, by taking in a plurality of pieces of images with their image contrast changed by changing the amount of retardation of two polarized lights generated in the differential interference contrast microscope, performing subtraction and addition to them, and by normalizing the obtained subtraction image by the addition image, only the image component in which the optical response character (also referred to as OTF: Optical Transfer Function) of the differential interference contrast microscope is convolved with the phase distribution of the phase object can be extracted. This technique uses the fact that when the amount of retardation of a polarized light is changed without moving the observation position, the image component corresponding to the amount of defocus presented in Japanese Laid-open Patent Publication No. 2008-102294 does not change. In greater detail, by performing subtraction of images obtained by changing the amount of retardation of the polarized light symmetrically (±θ), the image component corresponding to the amount of defocus is removed, to obtain only the image intensity distribution in which the phase distribution of the observed object and the optical response character of the differential interference contrast microscope are convolved. Meanwhile, Japanese Laid-open Patent Publication No. 9-15504 discloses that by deconvolution of the image intensity distribution calculated as described above using the optical response character of the differential interference contrast microscope, the phase distribution of the observed object can be obtained.

The value of the optical response character of the differential interference contrast microscope approaches 0 in the low-frequency band where the spatial frequency is close to 0 and in the frequency band around the cutoff frequency. For this reason, division by 0 may occur in the deconvolution process, but this issue can be improved by devising the Wiener filter. Japanese Laid-open Patent Publication No. 2006-300714 presented a challenged that, by such a solution, the accuracy decreases in obtaining the phase distribution of an object having a low gradient, and discloses that the challenge can be overcome by a partial integral process.

The inventor of the present invention newly found that, particularly in observing a biological sample, there are many parts having phase distribution with a low gradient in the nucleus and the like and a false image may be generated in performing the deconvolution process, and that noises may be linked in performing the integral process, due to a large number of granular tissues. Also newly found is that since the structure of the biological sample (a living tissue and cell colony) extends in the optical axis direction, unevenness in the field of view may be generated due to a subtle misalignment in the localize position of the Nomarski prism, and unevenness is generated in the observation area.

Hereinafter, a method for improvement in these new challenges and to obtain the phase distribution in the observation area of the biological sample with a good accuracy is explained with reference to FIG. 1.

First, an optical image of a biological sample formed by a microscope that converts phase distribution into image intensity distribution such as a differential interference contrast microscope is taken in while changing the image contrast in the image sensor, to form a plurality of pieces of images with different image contrasts (step S1 in FIG. 1 (image contrast image forming process)).

Then, based on the formed plurality of pieces of images, a component corresponding to the phase distribution of the biological sample and a component corresponding to other than the phase distribution of the biological sample are calculated. The component corresponding to other than the phase distribution of the biological sample includes, for example, a component according to the absorption of the biological sample, a component according to the illumination distribution, and the like. After that, by dividing the calculated component corresponding to the phase distribution by the component corresponding to other than the phase distribution, a normalized image of the component corresponding to the phase distribution (hereinafter, a normalized phase component image) is formed (step S3 in FIG. 1 (phase component image forming process)). Meanwhile, this procedure is disclosed in, for example, Japanese Laid-open Patent Publication No. 09-015504.

Next, the obtained normalized phase component image is broken down into a background component with the lowest spatial frequency, a refraction component formed by a light reflected on inside the biological sample, and a structure component with the highest spatial frequency formed by a light diffracted by the structure inside the biological sample. That is, the normalized phase component image is broken down in to a plurality of frequency components by the spatial frequency of the image (step S5 in FIG. 1 (spatial frequency breaking down process)).

Meanwhile, the unevenness of the field of view mentioned above is composed of, in terms of the spatial frequency, frequency components of four pitches at most in the observation area, and its influence is considered to be appear in the background component. In addition, in apart having phase distribution with a low gradient in the biological sample such as the nucleus has a frequency band of about one-tenth of the cutoff frequency of the microscope at most, and is detected as a refraction component. In addition, the fine structure of the biological sample such as the granular tissue has a higher frequency than these, and is detected as a structure component.

Furthermore, a deconvolution process is applied to each of the refraction component and the structure component being the image intensity distribution and the optical response character corresponding to each, and the phase distribution of the refraction component and the phase distribution of the structure component are calculated separately (step S7 in FIG. 1 (phase distribution calculating process)). Then, by compounding them, the phase distribution of the biological sample is calculated (step S9 in FIG. 1 (phase distribution of the biological sample compounding process)).

As described above, the normalized phase component image is broken down into three components, and furthermore, for the deconvolution process, two components, the refraction components and the structure components except the background components are used. For this reason, the influence of the unevenness of the field of view appearing in the background component can be suppressed. In addition, for each of the refraction component and the structure component, the deconvolution process is performed to a different optical response character corresponding to each. For this reason, the generation of a false image and link of noises can be suppressed. Therefore, according to this method, more accurate phase distribution of the biological sample can be obtained.

Meanwhile, when Fourier transformation is applied to the normalized phase component image and the result is broken down into three frequency components focusing only on the frequency, noise can be generated due to the breaking down. For this reason, in the method described above, it is desirable to use low-pass filtering for an averaging process of the image, when breaking down the normalized phase component image into the three components. For example, by applying the convolution process to the normalized phase component image a plurality of times by an averaging filter having a relatively large averaging area, an image of the background component is formed. Furthermore, by applying a convolution process to an image obtained by subtracting the image of the background component from the normalized phase component image a plurality of times by an averaging filter with a smaller averaging area than the background component, an image of the refraction component is formed. Lastly, by subtracting the image of the background component and the image of the refraction component from the normalized phase component image, an image of the structure component is formed. As described above, it is desirable to break down the normalized phase component image into the background component, the refraction component and the structure component, by applying the averaging process to the normalized phase component image by filters with different kernel sizes.

Meanwhile, when using a differential interference contrast microscope, the image contrast corresponding to the phase distribution in the direction perpendicular to the shear direction is not obtained, and it is difficult to calculate the phase distribution in the shear direction from the image intensity distribution of the image. For this reason, it is desirable to, by switching the shear direction, calculate phase distributions in two orthogonal shear directions by the method illustrated in FIG. 1, and to compound the obtained phase distributions. Meanwhile, a technique to compound two phase distributions obtained by switching the shear direction is also disclosed in Japanese Laid-open Patent Publication No. 9-15504.

In order to obtain differential interference contrast images in two shear directions by the method illustrated in FIG. 1 in step S1 for example, the shear direction needs to be switched by switching the Nomarski prism, or by rotating a single Nomarski prism. Even when the parallelism and the attachment angle of the Nomarski prism are adjusted, movement of the image by about several pixels occur due to the switching, and it is difficult to avoid the occurrence of misalignment in the calculated phase distributions. Then, when these phase distributions are compounded without correcting the misalignment, a wobble occurs in the compounded phase distribution. For this reason, when compounding phase distributions calculated in two orthogonal shear directions, it is desirable to detect the image movement occurring at the time of the switching of the shear direction and to correct the position before compounding these images.

Meanwhile, in the phase distribution calculated by the deconvolution process of the structure component, the distribution other than the structure extending in an approximately direction perpendicular to the shear direction becomes distribution corresponding to the object structure. For this reason, the similarity between two phase distributions of the structure component calculated by switching the shear direction becomes very high compared with the case of other components (the background component, the refraction component). It is desirable, using this characteristic, for example, to calculate the amount of misalignment in the images occurring at the time of switching the shear direction from the correlation between the two phase distributions of the structure component calculated in the two shear directions, and to use the calculated amount of misalignment to correct the misalignment in the two phase distributions of the biological sample calculated in the two shear directions before and after the switching. Accordingly, the wobble in the phase distribution after compounding may be suppressed. Meanwhile, the correlation can be obtained by, for example, the phase-only correlation. In addition, it is desirable that, the correction of the misalignment occurring due to the shear direction and compounding are performed, in FIG. 1, between step S7 and step S9.

The phase-contrast microscope and the differential interference contrast microscope are a microscope that is capable of observing living cells and tissues without dyeing, but when the observed object has a three-dimensionally complicated structure, a blurred image of living cells and tissues above and below the observation position gets into the observed image. Accordingly, image intensity distribution that is different from the actual structure of the observation position is generated, making it difficult to check the structure of the living cells and tissues, and to check the mutation and alteration. Hereinafter, a method for improvement in such a challenge and to obtain the phase distribution in the observation area in the biological sample with a better accuracy is explained with reference to FIG. 2-FIG. 7.

Generally, the optical response character OTF (Optical Transfer Function) is expressed by MTF·exp($2\pi i$·PTF). Here, MTF is a modulation transfer function (MTF: Modulation Transfer Function), and PTF is a phase transfer function (PTF: Phase Transfer Function). When the observed object is on the focus position of the optical system, and when the optical system is ideal, PTF=0 and hence OTF is MTF, and dependence is only on MTF. However, when the observed object deviates from the focuses position or when aberration occurs, PTF≠0 and hence, as OTF, MTF·exp($2\pi i$·PTF) needs to be used. In Japanese Laid-open Patent Publication No. 9-15504 mentioned above, in order to simplify the explanation, assuming that the observed object is on the focus position and that the optical system is ideal, OTF that is dependent on MTF only is used in performing the deconvolution process.

Meanwhile, FIG. 3 is a diagram illustrating OTF of the microscope when the observed object is on the focus position and that the optical system is ideal. FIG. 3 illustrates L1, L2 respectively representing OTF of a bright field microscope and a differential interference contrast microscope equipped with the same objective lens and condenser lens. Meanwhile, MTF of the bright field microscope is determined by the numerical aperture (hereinafter, described as NA) of the objective lens and the NA of the condenser lens, while MTF of the differential interference contrast microscope is determined by the product of MTF of the bright field microscope and sin($\pi \Delta f$). Meanwhile, here, $\Delta$ is the shear amount, and f is the spatial frequency. Such relationship between MTF of the bright field microscope and MTF of the differential interference contrast microscope is described in, for example, Japanese Laid-open Patent Publication No. 2008-102294.

In the biological sample having a three-dimensional structure, a part (structure C2) positioned on the focus position (Z in FIG. 4) of the observation optical system and a part (structure C1, C3) positioned on a position (+$\Delta$Z, -$\Delta$Z in FIG. 4) out of the focus position exist. Meanwhile, FIG. 4 is a schematic diagram in which the horizontal direction of the paper represents the position of the observed object in the plane vertical to the optical axis at a given position in the optical axis direction, and the thickness of the ellipse in the vertical direction represents the phase amount. When the deconvolution process is performed using OTF that is dependent on MTF only, as in Japanese Laid-open Patent Publication No. 9-15504, as illustrated in FIG. 5, the phase distribution corresponding to the part (structure C2) positioned on the focus position is reproduced, and at the same time, the phase distribution of the part (structure C1, structure C3) on the position out of the focus position is reproduced with a smaller phase amount than the phase distribution, affected by PTF. This is because, the part on the position out of the focus position has image intensity distribution obtained by convolution of its phase distribution and MTF·exp($2\pi i$·PTF), and originally, the deconvolution process is supposed to be performed using MTF·exp($2\pi i$·PTF), but the deconvolution process was performed using MTF.

On the other hand, when the deconvolution is performed by calculating PTF corresponding to the position out of the focus position by calculation and using MTF·exp($2\pi i$·PTF), the phase distribution corresponding to the part out of the focus position is reproduced, and the phase distribution of the part positioned on the focus position is reproduced with a smaller phase amount than its phase distribution, affected by PTF. This is because the part positioned on the focus position has image intensity distribution obtained by convolution of its phase distribution and MTF, and originally, the deconvolution process is supposed to be performed using MTF, but the deconvolution process was performed using MTF·exp($2\pi i$·PTF). That is, the phase distribution of the part positioned on the focus position becomes equivalent to the one obtained by convolution of the actual phase distribution with exp($-2\pi i$·PTF), and is hence reproduced with a small phase amount.

By using this characteristic, the phase distribution of the part (structure C2) positioned on the focus position and the phase distribution of the part (structure C1, C3) positioned out of the focus position in the observed object are separated.

Specifically, first, by the procedure of step S11 through step S17 in FIG. 2, the phase distribution of the refraction component and the phase distribution of the structure component are calculated using OTF in the focused state with respect to the observation plane illustrated in FIG. 3 (the state in which the focal plane of the optical system is positioned on the observation plane). Meanwhile, step S11 through step S17 are processes corresponding to step S1 through step S7 in FIG. 1. In step S17, the phase distribution (phase distribution B1 in FIG. 6) is calculated using OTF in the focused state with respect to the observation plane (that is, MTF).

Next, using OTF in the defocus state with respect to the observation plane (the state in which the focal plane of the optical system is on a position out of the observation plane), the deconvolution process is performed to the structure component obtained in step S15, to calculate the second phase distribution (phase distribution B2, B3 in FIG. 6) of the structure component (step S19 in FIG. 2 (second phase distribution calculating process)).

Here, OTF in the defocus status is OTF calculated from OTF on the focus position (that is, MTF) and PTF on a position out of the focus position (that is, PTF generated due to defocus), and is MTF·exp($2\pi i$·PTF). The phase distribution B2 in FIG. 6 is phase distribution of the structure component calculated using OTF on the position away from the focus position Z by $+\Delta Z$, and the phase distribution B3 in FIG. 6 is phase distribution of the structure component calculated using OTF on the position away from the focus position Z by $-\Delta Z$. Meanwhile, the phase distribution B1 in FIG. 6 is the phase distribution of the structure component calculated in step S17 using OTF on the focus position Z.

Furthermore, the second phase distribution calculated in step S19, and the phase distribution of the structure component being the phase distribution in the focused state with respect to the observation plane already calculated in step S17 are compared (step S21 in FIG. 2 (phase distribution comparing process)).

As mentioned above, in the phase distribution obtained by deconvolution using the OTF in the focused state, the phase amount of the part on the focus position of the biological sample is calculated large, and in the phase distribution obtained by deconvolution using OTF in the defocus state, the phase amount of the part positioned on the specific position out of the focus position of the biological sample is calculated large. Using this characteristic, in the comparing process, from the phase distribution image, a binary image assuming the part on the focus position as 1 and the part on the position out of the focus position as 0 is formed, and according to it, the area out of the focus position (for example, the area out of the depth of focus of the microscope) is identified. In the example of FIG. 6, a binary image assuming the part in which the structure C2 is positioned as 1 and the part in which the structures C1, C3 are positioned as 0 is formed.

Meanwhile, PTF changes corresponding to the (defocus) amount of being away from the focus position, but even with the same amount of defocus, the influence that PTF gives to OTF is different depending on the spatial frequency of the object. In FIG. 7, OTF in the focused state is represented by the solid line, and OTF in the defocus state is represented by the broken line. More specifically, L1d illustrated in FIG. 7 represents OTF of the bright field microscope in the defocus state. Meanwhile, L2dr, L2di illustrated in FIG. 7 respectively represent the real part, the imaginary part of OTF of the differential interference contrast microscope in the defocus state, In the same manner as in FIG. 3, L1, L2 illustrated in FIG. 7 are OTF of the bright field microscope and the differential interference contrast microscope in the focus state.

As illustrated in FIG. 7, since the influence of PTF on OTF in the area in which the spatial frequency of the object is relatively high (that is, the difference between OTF in the focused state and OTF in the defocus state) becomes large, in forming a binary image by separating the part on the focus position and the position out of the focus position, it is desirable to use the structure component with a high spatial frequency, as described above. Accordingly, it becomes possible to make the change of the phase amount with respect to the amount of defocus larger than in the case of using other components, and to increase the sensitivity of the separation.

when the comparing process in step S21 is completed, based on the comparison result, the phase distribution in which blurring due to defocus has occurred is removed from the phase distribution of the structure component calculated in step S17 (step S23 in FIG. 2 (blurred phase distribution removing process)).

Here, first, by obtaining the product of the second phase distribution of the structure component calculated in step S19 and the binary image formed in step S21, the phase distribution of the structure component on the position out of the focus position is extracted. After that, by applying the convolution process to the extracted phase distribution with OTF of the defocus state, the phase distribution of the structure component in which blurring due to defocus has occurred is calculated. Furthermore, the calculated phase distribution of the structure component in which blurring has occurred is subtracted from the phase distribution of the structure component calculated in step S17. Accordingly, the phase distribution of the structure component of the object positioned on the focus position is separated and extracted.

Lastly, the phase distribution of the structure component extracted in step S23 and the phase distribution of the refraction component calculated in step S17 are compounded, to calculate the phase distribution of the biological sample (step S25 in FIG. 2 (phase distribution of the biological sample compounding process)).

As described above, by removing the interfusion of the blurred image of the structure positioned above and below the observation position, it becomes possible to recognize the structure of the observation position more accurately. Therefore, according to the method illustrated in FIG. 2, the phase distribution of the biological sample in the observation area can be obtained with a better accuracy, and therefore, the three-dimensional structure of the cell and tissue can be inspected with a better accuracy without dyeing. In addition, the phase distribution can be reproduced with a good accuracy even when the biological sample has a three-dimensionally complicated structure.

Meanwhile, in FIG. 2, for the convenience of explanation, the expressions the focus position and the position out of the focus position are used. Since the change of the reproduced phase distribution is too small with respect to the change of PTF, it is impossible to separate the phase distribution on the position within the depth of focus from the focus position (observation plane). For this reason, more strictly, according to the method illustrated in FIG. 2, the blurred phase distribution on the position corresponding to the amount of defocus exceeding the depth of focus can be separated.

The method illustrated in FIG. 1 and FIG. 2 is a method to take in a plurality of images of the biological sample and a certain Z position in the optical axis direction, break down the normalized phase component image formed from those images into the background component, the refraction component and the structure component, and perform phase reproduction of the biological sample from the refraction component and the structure component. Especially the method illustrated in FIG. 2 is to reproduce the phase distribution with the influence from the object part on the position out of the Z position removed, by performing the deconvolution process while changing OTF without changing the Z position. That is, the method illustrated in FIG. 2 described above is a method to reproduce the phase distribution of the biological sample for which a certain Z position is the focus position, from only the image obtained at the certain Z position.

Meanwhile, Japanese Laid-open Patent Publication No. 2008-111726 discloses a technique to compare phase distributions reproduced from the normalized phase component image or the phase component image at respective Z positions and to make the Z position at which the contrast of the phase component image becomes largest or the Z position at which the value of the phase amount of the reproduced phase distribution becomes largest the focus position for object. The method presented in Japanese Laid-open Patent Publication No. 2008-111726 is good as a method to detect the structure on the surface of metal or silicon wafers. However, since only the phase distribution of one Z position for each pixel can be obtained in this method, when this method is applied without change to an object having three-dimensional overlap such as living cells and tissues, it is impossible to obtain the phase distribution of the biological sample having a three-dimensional structure.

Therefore, hereinafter, a method to reproduce the phase distribution of a biological sample for which a certain Z position is focus position, from images obtained at a plurality of Z positions, to obtain the phase distribution of a biological sample having a three-dimensional structure is explained with reference to FIG. 8.

First, the Z position (that is, the focal plane) is set on the Z position of interest (that is, the observation plane), and the phase distribution of the phase distribution of the refraction component and the phase distribution of the structure component are calculated by the procedure of step S31 through step S37. Meanwhile, step S31 through step S37 are processes corresponding to step S1 through step S7 in FIG. 1. Meanwhile, in step S37, the phase distribution is calculated using OTF in the focused state with respect to the observation plane illustrated in FIG. 3 (that is, MTF).

Figure 8:
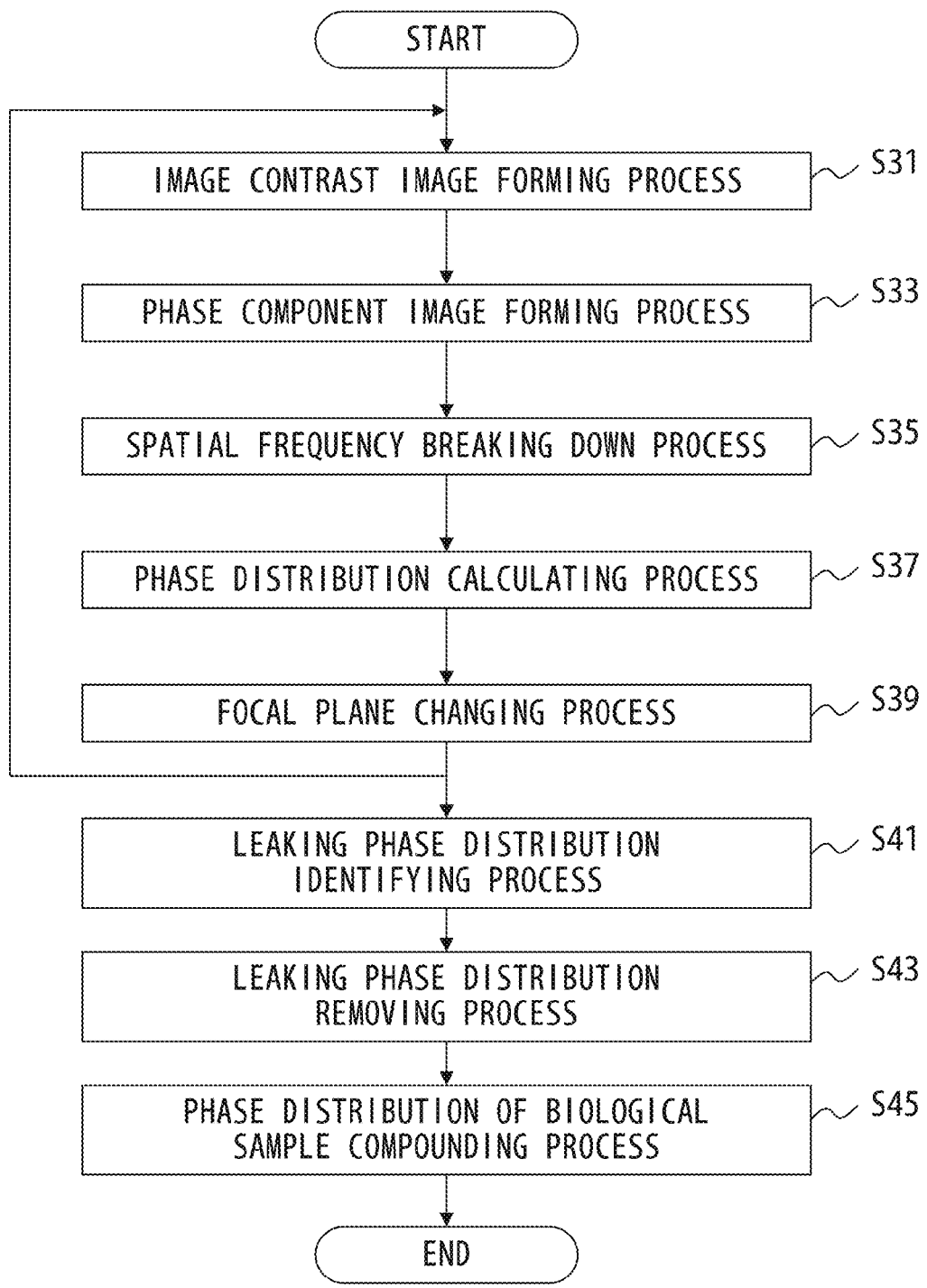
FIG. 8 is a yet another flowchart of a phase distribution measuring method according to an embodiment of the present invention.

Next, the Z position is moved (step S39 in FIG. 8 (focal plane changing process)). That is, the focal plane of the objective lens is moved in the optical axis direction with respect to the observation plane. After that, again, the processes of step S31 through step S37 are executed. Meanwhile, the processes of step S31 through step S39 are performed repeatedly, at least, to a position Z1 being the Z position of interest, a position Z2 moved in the positive direction from the position Z1, a position Z3 moved in the negative direction from the position Z1. That is, they are performed at least at the Z position of interest and adjacent Z positions above and below it.

After that, the phase distributions of the structure component calculated at respective Z positions (focal plane) is compared, and the phase distribution leaking from the structure of the biological sample exiting above and below the(certain) Z position into the(certain) Z position is identified (step S41 in FIG. 8 (leaking phase distribution identifying process)).

Figure 9:
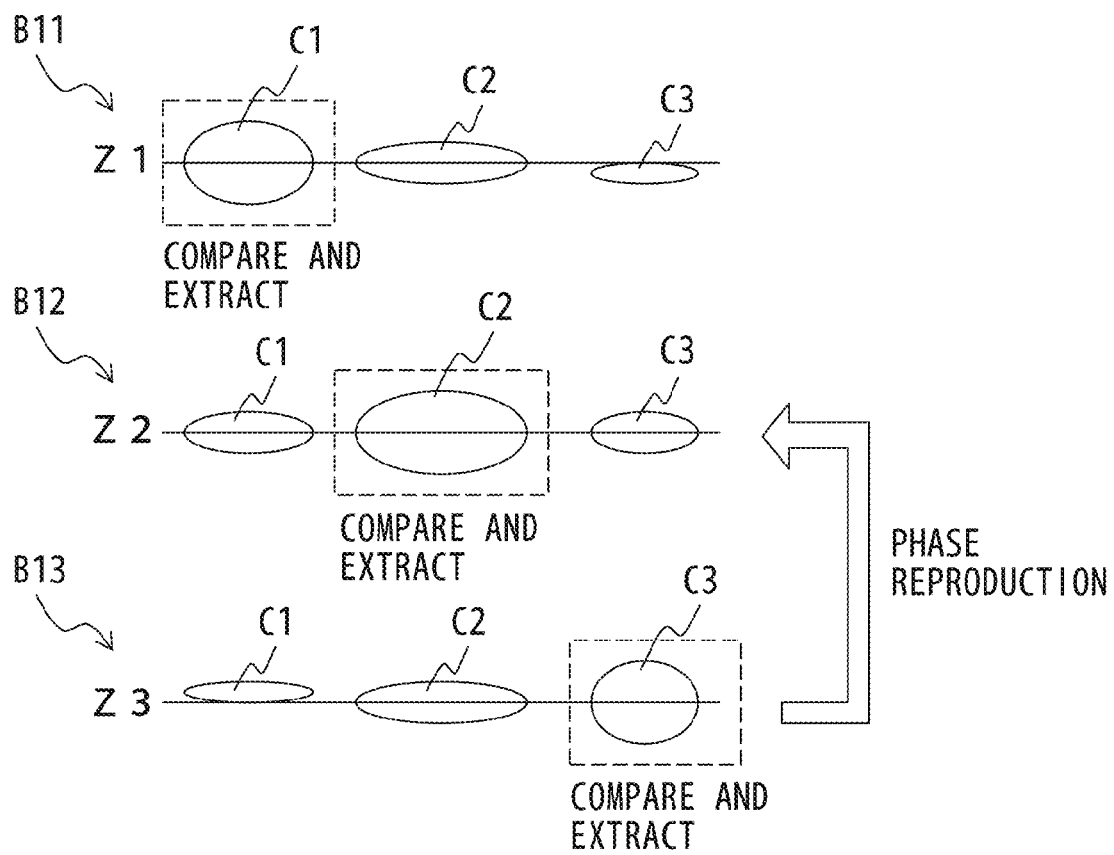
FIG. 9 is a diagram for illustrating another example of a method to reproduce phase distribution in which blurring occurred due to defocusing.

In step S41, first, for each Z position, the area in the XY plane orthogonal to the optical axis at which the phase amount of the structure component of the Z position becomes larger than the phase amount of the structure component at adjacent Z positions above and below is extracted as a part to determine the Z position as the focus position. The reason to use the phase distribution of the structure component here is that, since the phase distribution of the structure component has a character of changing more largely than the phase distribution of the refraction component when defocus amount is changed, it becomes possible to detect the part to be the focus position more accurately compared with the case of using the phase distribution after compounding that includes the phase distribution of the refraction component, or the phase distribution of the refraction component. Meanwhile, phase distributions B11, B12, B13 in FIG. 9 are phase distributions of the structure component calculated using OTF that is depending only on OTF (that is, MTF) at the position Z1, position Z2, position Z3, respectively.

In step S41, after that, for each Z position, OTF is calculated in view of PTF generated by defocus with the Z position and the adjacent Z positions above and below the Z position. Then, for each Z position, the convolution process is performed to the phase distribution of the area extracted from the phase component of the structure component, using OTF calculated in view of PTF. Accordingly, the phase component detected as a blurred image at adjacent Z positions above and below, in other words, the phase distribution leaking from the structure of the biological sample existing above and below each Z position into each Z position is identified.

After that, the phase distribution leaking into each Z position identified in step S41 is removed from the phase distribution of the structure component of each Z position (step S43 in FIG. 8 (leaking phase distribution removing process)). This is realized by subtracting the phase distribution leaking into each Z position from the phase distribution of the structure component of each Z position.

Lastly, the phase distribution of the structure component from which the phase distribution leaking into Z position calculated in step S43 is removed and the phase distribution of the refraction component are compounded, to calculate the phase distribution of the biological sample (step S45 in FIG. 8 (the phase distribution of the biological sample compounding process)).

As described above, according to the method illustrated in FIG. 8, unlike the method presented in Japanese Laid-open Patent Publication No. 2008-111726, it is possible to remove the interfusion of the blurred image of the structure positioned above and below the observation position. For this reason, it becomes possible to recognize the structure at the observation position more accurately. Therefore, according to the method illustrated in FIG. 8, since the phase distribution in the observation area of the biological sample can be obtained with a good accuracy, the three-dimensional structure of cells and tissues can be inspected with a better accuracy without dyeing. In addition, even when the biological sample has a three-dimensionally complicated structure, the phase distribution can be reproduced with a good accuracy.

The method illustrated in FIG. 8 can be used together with the method illustrated in FIG. 2, and by using these methods together, it becomes possible to further reduce the influence of the blurred image. In addition, as mentioned above, according to both the method illustrated in FIG. 2 and the method illustrated in FIG. 8, it is possible to extract only the phase distribution in the depth of focus by removing the phase distribution overlapped as the blurred image on the Z position of interest from outside the Z position of interest. For this reason, by obtaining the depth of focus by calculation or comparison measurement, and by dividing the phase distribution in the depth of focus by the depth of focus, the refraction index distribution at each Z position of the biological sample can be obtained. Furthermore, it is also possible to obtain the three-dimensional refraction index distribution of the biological sample by combining the refraction index distributions calculated for each Z position.

Meanwhile, as a method to remove the blurred image of the focused part at a different Z position from the image of the Z position, there is a method disclosed in Non-patent document 1 (David A. Argard, Y. Hiraoka, Peter Shaw, John W. Sedat "Methods in Cell biology", Vol 30(1989)). This method is known as a method, when using a fluorescent microscope, to remove the fluorescence leaking from the Z position other than the focus position of interest. In addition, this method is also known as having a bad affinity with observation methods other than the fluorescent microscope. The reason for it is that, for a fluorescent image, when the focal shift occurs, blurring is generated in the image in accordance with the focal shift, but in observation methods other than the fluorescent microscope, the formed image has a plurality of components, and the change in the image intensity of each component with the focal shift is different. For this reason, it is difficult to apply Non-patent document 1 to a microscope such as the differential interference contrast microscope and the phase-contrast microscope that converts the image intensity into phase distribution.

Hereinafter, the techniques of the method illustrated in FIG. 8 and Non-patent document 1 are compared, and their similarity and difference are explained. First, in the method illustrated in FIG. 8, the normalized phase component image is formed. The normalized phase component image is an image composed of an image signal in which the optical response character is convoluted with the phase distribution of the observed object, and has the same characteristics as the image characteristics of the fluorescent microscope. For this reason, the techniques of the method illustrated in FIG. 8 and Non-patent document 1 are similar with regard to the image characteristics. Meanwhile, in the method illustrated in FIG. 8, the normalized phase component image is broken down into the respective components of the background, refraction and structure. This is because, in the method illustrated in FIG. 8, it is taken into consideration that the background component is not relevant to the focal shift, that the refraction component has phase distribution that changes moderately and is shared by a plurality of Z positions and is insusceptible to the focal shift, and that the structure component is susceptible to the focal shift and a blurred image is easily overlapped on a different Z position. With this regard, the method illustrated in FIG. 8 and Non-patent document 1 are significantly different.

Hereinafter, examples of the phase measurement method described above are specifically explained.

Embodiment 1

The configuration of a phase measurement apparatus to execute the phase measurement method described above is explained, with reference to FIG. 10.

The microscope system 100 illustrated in FIG. 10 is a phase measurement apparatus to execute the phase measurement method described above, and includes a microscope 1, a computer 20 that controls the microscope 1, a plurality of drive mechanisms (drive mechanism 21, drive mechanism 22, drive mechanism 23, drive mechanism 24) that derive the microscope 1, and a monitor 25 that displays the image of a biological sample S. Meanwhile, the computer 20 includes at least with the configuration that a general computer has, such as a memory, a processor and the like, and the processing by the computer 20 described later is executed by the processor.

The microscope 1 is a differential interference contrast microscope that projects the structure of the biological sample S such as a cultured cell upon the light receiving surface of the image sensor as image intensity distribution, and is configured as an inverted microscope. More specifically, the microscope 1 includes an illumination system, a stage 8, an imaging system, and a CCD camera 13 including an image sensor.

The stage 8 is an electric stage on which the biological sample S is placed, and is configured to be moved in the optical axis direction by the drive mechanism 22 according to the instruction from the computer 20. The illumination system includes a light source 2, a lens 3, a field stop 4, an image contrast changing unit 5, a Nomarski prism 6 and a condenser lens 7, and the imaging system includes an objective lens 9, a Nomarski prism 10, an analyzer 11, and a tube lens 12. Here, the numerical aperture (NA) of the condenser lens 7 is, for example, 0.55. The objective lens 9 is a water immersion objective lens, and the magnification of the objective lens 9 is 60× for example, and the numerical aperture (NA) is 1.2.

The light emitted from the light source 2 is converted into a linear polarized light in the image contrast changing unit 5 in which it enters through the lens 3 and the field stop 4, separated into the ordinary light and extraordinary light in the Nomarski prism 6, and is delivered on the biological sample S placed on the stage 8 by the condenser lens 7. The ordinary light and extraordinary light that have passed through the biological sample S is compounded in the Nomarski prism 10 to which they enter through objective lens 9, and an image is formed on the light receiving surface of the CCD camera 13 by the analyzer 11 and the imaging lens 12. A differential interference contrast image is obtained as described above.

Here, the image contrast changing unit 5 has a polarizer 5a and a quarter wave plate 5b, and is a phase modulator adopting the Senarmont method, in which the phase of the linear polarized light is changed and converted into elliptical polarized light by the rotation control of the polarizer 5a by the drive mechanism 24 according to the instruction from the computer 20. In the microscope system 100, by the computer 20 controlling the image contrast changing unit 5 through the drive mechanism 24, the image contrast of image intensity distribution projected onto the CCD camera 13 by the microscope 1 will be changed continuously. In addition, the image contrast can also be changed discretely using a stepping motor and the like.

Meanwhile, the Nomarski prism 6, the Nomarski prism 10 are placed on the pupil position or its conjugate position of the condenser lens 7, the objective lens 9, respectively. In the microscope system 100, rotation control by the drive mechanism 21, the drive mechanism 23 is applied to the Nomarski prism 6 and the Nomarski prism 10 according to the instruction from the computer 20, to switch the shear direction.

That is, the computer 20 functions as a control unit that controls the CCD camera 13 and the image contrast changing unit 5 so as to obtain a plurality of pieces of images with different image contrasts, and also controls the Nomarski prism 6 and the Nomarski prism 10 to switch the shear direction. In addition, since the computer 20 is capable of moving the stage 8 in the optical axis direction through the drive mechanism 22, it also functions as a focus position control unit that changes the focal plane in the optical axis direction. Furthermore, as described later, the computer 20 also functions as a calculating unit that calculates the phase distribution of the biological sample from a plurality of pieces of images with different image contrasts obtained by the control the computer unit 20 performs.

Next, the phase measurement method by the microscope system configured as described above is explained.

First, the computer 20 makes the drive mechanism 21, the drive mechanism 23 rotate the Nomarski prism 6, the Nomarski prism 10 so that the shear direction becomes 45° direction with respect to the reference direction on the light receiving plane of the CCD camera 13. After that, the computer 20 changes retardation to ±θ, 0 in order by making the drive mechanism 24 rotate the polarizer 5a and takes in three differential interference contrast images I1 (−θ), I1 (0), I1(θ) with different image contrasts from the CCD camera 13.

Next, the computer 20 makes the drive mechanism 21, the drive mechanism 23 rotate the Nomarski prism 6, the Nomarski prism 10 by 90° to set the shear direction as −45° direction with respect to the reference direction on the light receiving plane of the CCD camera 13. After that, the computer 20 changes retardation to ±θ,0 in order by making the drive mechanism 24 rotate the polarizer 5a, and takes in three differential interference contrast images I2(−θ), I2(0), I2(θ) with different contrasts from the CCD camera 13.

Meanwhile, the rotation of the polarizer 5a by the drive mechanism 24 is controlled so that offset correction is performed to the gap in the amount of retardation generated according to the rotation of the Nomarski prism using a value measured in advance, so that the retardation generated in the phase modulator (image contrast changing unit 5) becomes ±θ,0 regardless of the direction of the Nomarski prism.

Next, the computer 20 forms the normalized phase component image for each shear direction, by performing the following calculation using the obtained differential interference contrast images. Here, Def1, Def2 are normalized phase component images.

$$Def1=\{I1(\theta)-I1(-\theta)\}/\{I1(\theta)+I1(-\theta)-I1(0)\}$$

$$Def2=\{I2(\theta)-I2(-\theta)\}/\{I2(\theta)+I2(-\theta)-I2(0)\}$$

After that, the computer 20 applies an averaging process several times to each of the normalized phase component images Def1, Def2 using an averaging filter with the averaging area (kernel size) of 100×100, to form images BG1, BG2 of the background component. Furthermore, the images BG1, BG2 of the background component are subtracted from each of the normalized phase component images Def1, Def2. Each of the images (Def1−BG1), (Def2−BG2) from which disturbances such as unevenness of the field of view are removed is obtained accordingly. An averaging process is performed several times to the images (Def1−BG1), (Def2−BG2) using an averaging filter with the averaging area (kernel size) of 20×20, to form images GR1, GR2 of the refraction component. Furthermore, the images BG1, BG2 of the background component and the images GR1, GR2 of the refraction component are subtracted from the normalized phase component images Def1, Def2, to form images ST1(=Def1−BG1−GR1), ST2(=Def2−BG2−GR2) of the structure component.

Next, the computer 20 performs a deconvolution process to the images ST1, ST2 of the structure component using OTF (L2 in FIG. 3) in the focused state of the differential interference contrast microscope illustrated in FIG. 3, to calculate phase distributions PhS1, PhS2 of the structure component representing the fine structure of the object.

Meanwhile, in the optical response character illustrated in FIG. 3, its value approaches 0 in two bands, the band in which the frequency is 0 and the band in which the frequency is the cutoff frequency. Since division by 0 occurs in the deconvolution process for this reason, the Wiener method is adopted to avoid division by 0. In the images ST1, ST2 of the structure component, the image component in the band in which the frequency is close to 0 is small, and therefore, the calculation error may be reduced using the Wiener method.

The computer 20 calculates the relative position misalignment amount between images generated due to the switching of the shear direction of the Nomarski prism from phase distributions PhS1, PhS2 of the structure component. The phase distributions PhS1, PhS2 of the structure component are phase distributions of the structure component obtained of the same object (biological sample S) before and after changing the shear direction of the Nomarski prism. For this reason, the phase distributions are similar except for the phase distribution related to the approximately vertical structure with respect to the shear direction of each. Therefore, by applying the phase-only correlation to the phase distributions PhS1, PhS2 of the structure component, the position misalignment amount (δx, δy) between two images can be calculated.

Furthermore, the computer 20 performs the deconvolution process to the images GR1, GR2 using OTF illustrated in FIG. 11 instead of OTF illustrated in FIG. 3, in view of that the images GR1, GR2 of the refraction component has a moderate change of the phase of the biological sample. Accordingly, the phase distributions PhG1, PhG2 of the refraction component that represents a moderate phase change are calculated.

Meanwhile, OTF (L3 in FIG. 11) corresponding to the refraction component in the focused position is calculated as sin(πΔf), based on that MTF of the differential interference contrast microscope is a product of MTF and sin(πΔf) of the bright field microscope, and that the refraction component is a lower frequency component compared with the structure component, and under that condition, MTF of the bright field microscope may be regarded as 1 as represented by L1 in FIG. 3.

When the phase distributions PhS1, PhS2 of the structure component and the phase distributions PhG1, PhG2 of the refraction component are calculated, the computer 20 compounds them to calculate phase distributions Ph1, Ph2 of the observed object (biological sample S). Meanwhile, the phase distributions Ph1, Ph2 of the observed object is phase distributions corresponding to images (Def1−BG1), (Def2−BG2) of image intensity distribution from which disturbances such as unevenness of the field of view are removed, and is calculated by the following formulas.

$$Ph1=PhS1+PhG1$$

$$Ph2=PhS2+PhG2$$

Lastly, to exclude the influence of the shear direction, the phase distributions Ph1, Ph2 of the observed object obtained in orthogonal shear directions are compounded. The compounding is performed after correcting phase distributions Ph1, Ph2 using the position misalignment amount ($\delta x$, $\delta y$) between images. Accordingly, the phase distribution Ph of the biological sample from which the influence of the shear direction is excluded can be obtained.

It is expected that phase distribution of the part existing in the vicinity of focused position (within depth of focus) and blurred phase distribution of the part existing on a position slightly out of the focused position (for example, a position away by about ±2 μm) is included in the phase distribution Ph of the biological sample obtained by the method described above. In order to remove such blurred phase distribution, the computer 20 further performs the following calculation.

First, the computer 20 performs the deconvolution process using OTF in a state defocused by about 2 μm from the focal plane, as illustrated in FIG. 7, to images ST1, ST2 of the structure component, and calculates phase distributions PhSd1, PhSd2 of the structure component.

Next, the computer 20 compares the phase distributions PhSd1, PhSd2 of the structure component calculated using OTF in the defocus state, and the phase distributions PhS1, PhS2 of the structure component calculated using OTF in the focused state. In the phase distributions PhSd1, PhSd2 of the structure component calculated using OTF in the defocus state by about 2 μm, blurring in the phase distribution of the object existing on the defocused position is reduced, and the phase distribution of the object existing on the defocused position is calculated as a larger value than in the phase distributions PhS1, PhS2 of the structure component. In view of this, the part in the vicinity of the focus position and the part away from the focused position by about 2 μm are identified, and phase distributions PhSP1, PhSP2 of the part on the position away by about 2 μm from the focus position are extracted.

Furthermore, the computer 20 performs the convolution process using OTF in defocus state to the extracted phase distributions PhSP1, PhSP2, to calculate phase distributions PhSR1, PhSR2 in which blurring at the focus position is reproduced.

Lastly, the computer 20 subtracts the phase distributions PhSR1, PhSR2 in which blurring is reproduced, from the phase distributions PhS1, PhS2 of the structure component. Accordingly, the phase distribution of the structure component existing in the vicinity of the focus position is calculated more accurately.

Figure 12A:
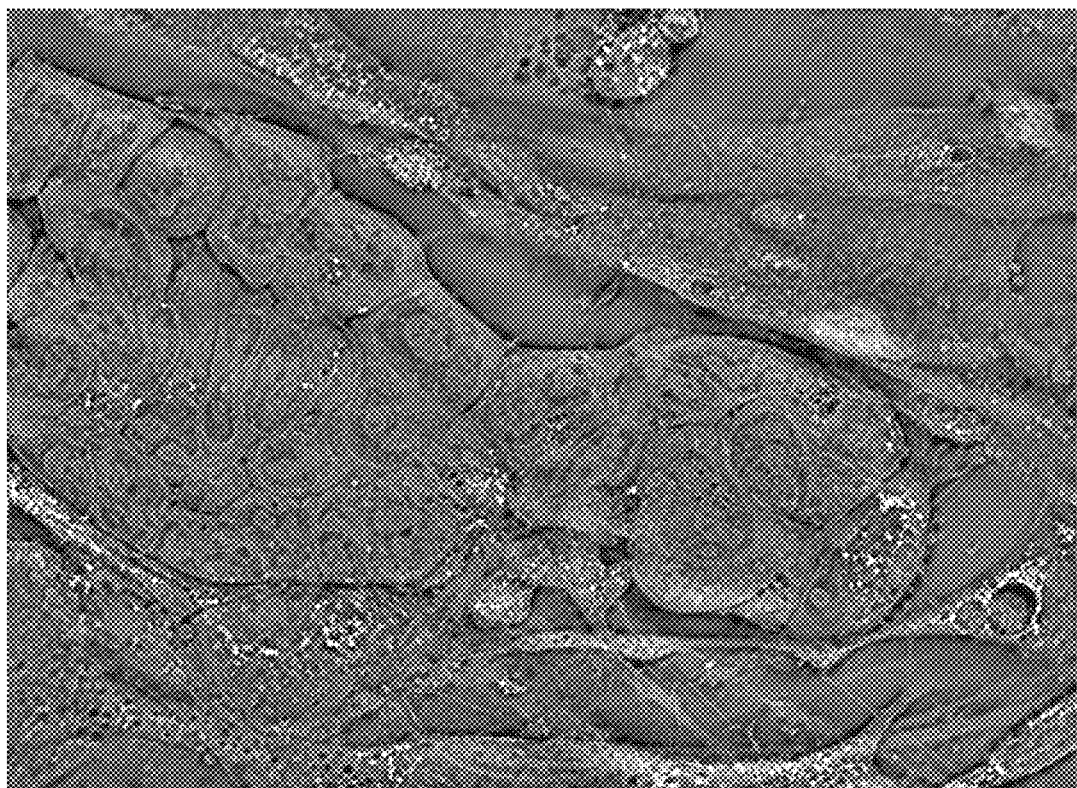
FIG. 12A is a diagram illustrating the phase distribution of iPS cells obtained by the microscope system illustrate in FIG. 10.
Figure 12B:
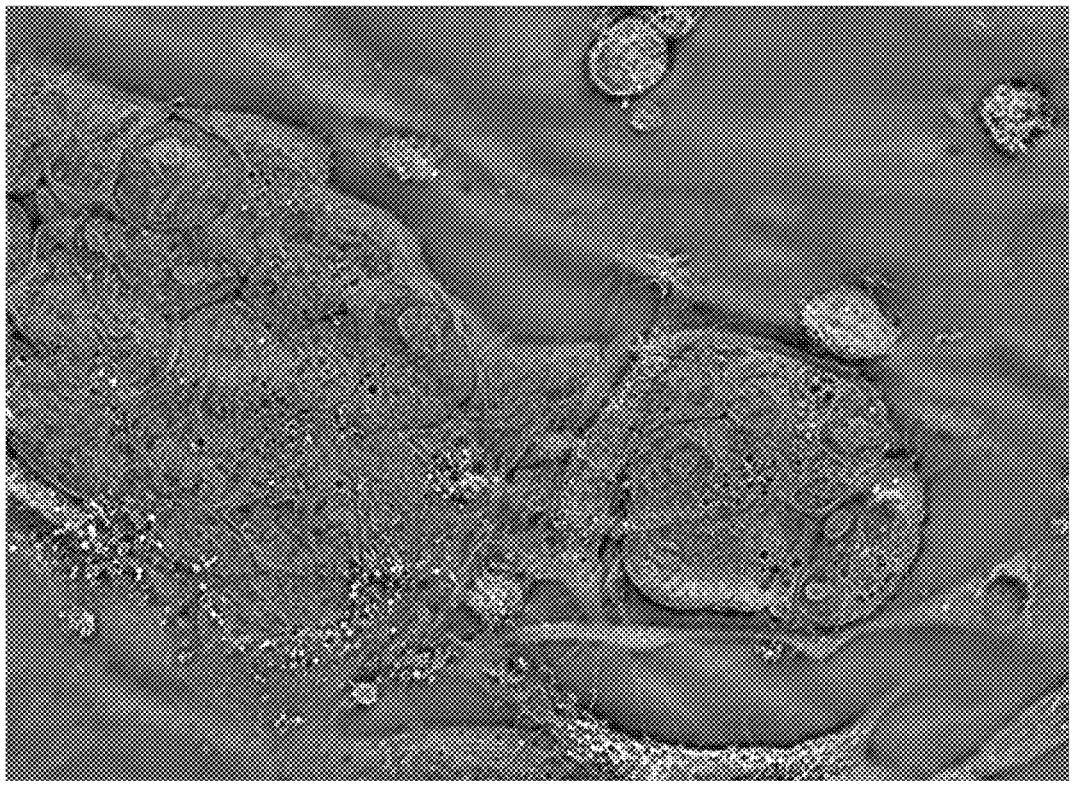
FIG. 12B is a diagram illustrating the phase distribution of iPS cells obtained by the microscope system illustrated in FIG. 10, when the observation position is shifted upward by 3 μm in the optical axis direction from FIG. 12A.
Figure 12C:
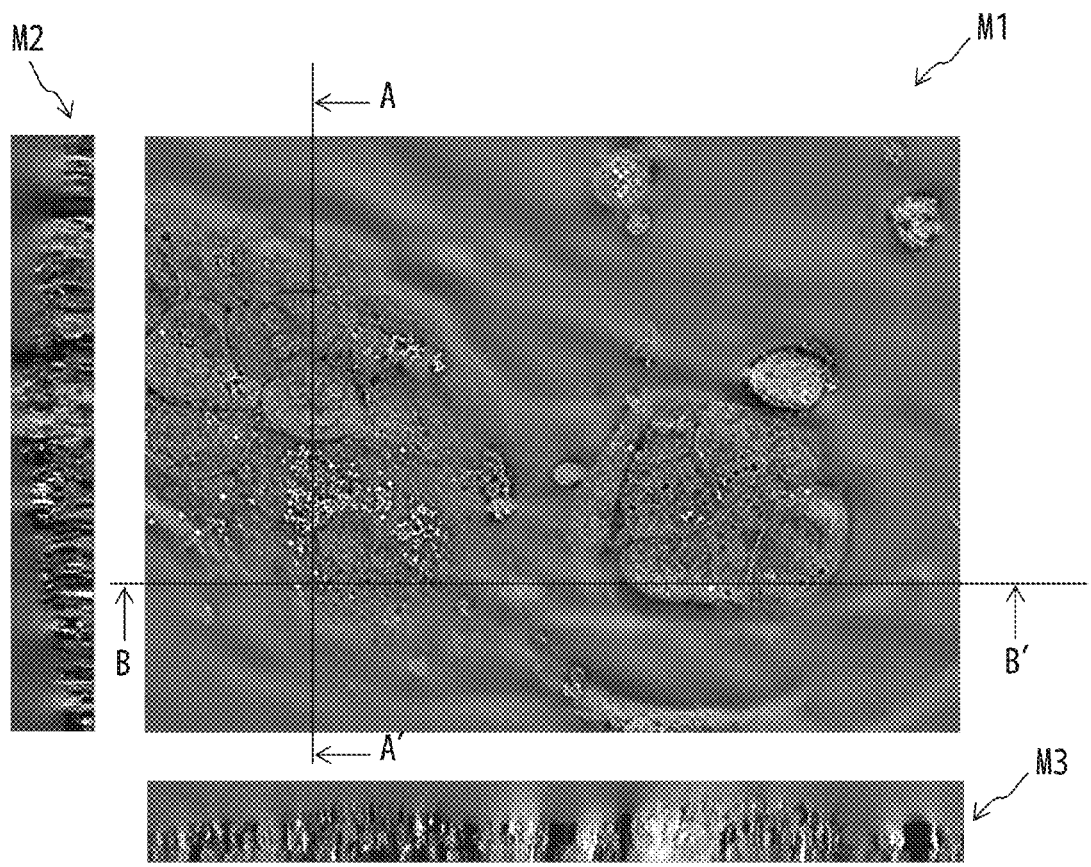
FIG. 12C is a diagram illustrating the phase distribution of iPS cells obtained by the microscope system illustrated in FIG. 10, when the observation position is shifted upward by 3 μm in the optical axis direction from FIG. 12B.

FIG. 12A, FIG. 12B, and FIG. 12C are a part of a plurality of phase distribution images obtained by measuring the phase distribution of iPS cells of a mouse in a culture solution with the microscope system 100 while changing the observation position in the optical axis direction in steps of 0.5 μm. More specifically, the phase distribution of the iPS cells of a mouse in a culture solution is observed using a water immersion object lens of 60×, NA=1.2, illuminated by a condenser lens of NA=0.55. Meanwhile, FIG. 12A is a phase distribution image measured at the deepest observation position, FIG. 12B is a phase distribution image measured at an observation position positioned 3 μm above the observation position in FIG. 12A, and FIG. 12C is a phase distribution image measured at an observation position positioned further 3 μm above the observation position in FIG. 12B. In addition, FIG. 12C presents, in addition to an image M1 viewed from the optical axis direction, an image M2 and an image M3 of the cross-sectional diagrams on the cross-section A-A' and on the cross-section B-B' presented in the image M1. Meanwhile, the image M2 and the image M3 are images generated from a plurality of phase distribution images obtained with the change in steps of 0.5 μm in the optical axis including images illustrated in FIG. 12A through FIG. 12C.

Meanwhile, the observation wavelength in FIG. 12A through FIG. 12C is 550±30 nm, a halogen lamp and an interference filter are placed in the light source 2, and the illumination light is made to be quasi-monochromatic in the wavelength range of 550±30 nm by the interference filter.

In FIG. 12A, a colony of the iPS cells is observed in the center part of the image, and differentiated other cells are observed in the surrounding part. Furthermore, in the colony of the iPS cells, it is also observed that apart in which cells constituting the colony are closely spaced, and apart in which cells are spaced relatively widely exist.

Furthermore, in FIG. 12B in which the observation position is 3 μm higher compared with the FIG. 12A, the existence of the colony of the iPS cells positioned on the center is observed, but the existence of differentiated cells that are positioned in the surrounding part in FIG. 12A is not observed. According to this difference, the thickness of the cell can be recognized. In addition, in FIG. 12B, the overlap of differentiated cells in the colony of the iPS cells positioned in the center part is observed, making it possible to recognize that a part of iPS cells is differentiated and is laid in the upper part of the colony. Furthermore, comparing FIG. 12A and FIG. 12B, the shapes of the cells that form the colony of the iPS cells are different. According to this, it is recognized that, in FIG. 12A and FIG. 12B, cells at different positions in the optical axis direction in the cell group forming the colony are observed.

Also in FIG. 12C in which the observation position is 3 μm higher compared with FIG. 12B (that is, compared with FIG. 12A, the observation position is 6 μm higher), the colony of the iPS cells and differentiated cells laid in the upper part of the colony can be observed. In FIG. 12C, the existence of cells forming the colony of the iPS cells that are different from the cells observed in FIG. 12A and FIG. 12B is observed.

As described above, from the phase distribution image obtained by the microscope system 100, information related to the height of the colony and the thickness of each cell forming the colony can by be obtained, and the state of the cell at each position in the optical axis position can also be checked. Specifically, referring to FIG. 12A through FIG. 12C, it is understood that the height (thickness) per cell is several μm or more, not only for the iPS cells but also for the differentiated cells.

Meanwhile, since it is expected that organelle in cells also have a size of μm order, and that cells and cell organelles change continuously, it follows that, when the phase distribution is measured while changing the observation position, detection overlaps continuously at a plurality of observation positions. By obtaining correlation (similarity) between phase distribution measured at a certain observation position and phase distributions measured at preceding and subsequent observation positions, the continuity of the phase distributions measured at each observation position can be distinguished. Using this continuity, by continuously connecting the phase distributions, the phase distribution of the cells and cell organelle can be obtained accurately. In addition, by dividing the phase distribution by the internal of the observation positions, relative refraction index distribution of cell and cell organelle at each position can also be obtained.

As described above, according to the microscope system 100 of this embodiment, since the accurate phase distribution of the iPS cell can be obtained, from the phase reproduction result of the iPS cells, the inner structure of the cultured iPS cell can be measured as phase distribution. In addition, the normal cell and the mutated cell inside the colony can also be determined. Furthermore, the undifferentiated state of the iPS cell can also be identified. That is, it is possible to evaluate the cell state (the morphological change, colony change, dead cell distribution, adherence between cells) in the colony, the degeneration of cells due to differentiation. Meanwhile, without limitation to the iPS cells, the same applies to ES cells.

Embodiment 2

A microscope system 101 illustrated in FIG. 13 is a microscope system including a microscope 1a, and is a phase measurement apparatus that executes the phase measurement method described above in the same manner as the microscope system of Embodiment 1. The microscope system 101 differs from the microscope system 100 in including an LED light source 31 and an LED light source 32 instead of the light source 2, a phase modulating unit 30 instead of the image contrast changing unit 5, and a drive mechanism 26 instead of the drive mechanism 24. Other configurations are the same as in the microscope system 100.

The LED light source 31 and the LED light source 32 are, for example, a single-color LED light source. In the microscope system 101, the computer 20 controls the light emission of the LED light source 31 and the LED light source 32 through the drive mechanism 26.

Meanwhile, it is also possible to use a white-color LED light source. In that case, in the same manner as in Embodiment 1, it is made to be quasi-monochromatic by further placing an interference filter.

The phase modulating unit 30 includes two polarizers (polaraizer 33, polarizer 34) that are rotatable with respect to the optical axis, a beam splitter 35 being a light compounding member that compounds the light from the LED light source 31 and the light from the LED light source 32 and to emit it in the direction of the optical axis of the lens 3, and a quarter wave plate 36 placed with its optic axis facing a certain direction. The beam splitter 35 includes, for example, a half mirror.

The polaraizer 33, the polaraizer 34 are placed between the light source 31 and the beam splitter 35, and between the LED light source 32 and the beam splitter 35, respectively. The polaraizer 33 and the polaraizer 34 are same as the polaraizer 5a in FIG. 10 in that rotation control of them is applied by the computer 20 via a drive mechanism (here, the drive mechanism 26), and that they function as a phase modulator adopting the Senarmont method together with a quarter wave plate (here, the quarter wave plate 36).

Figure 14:
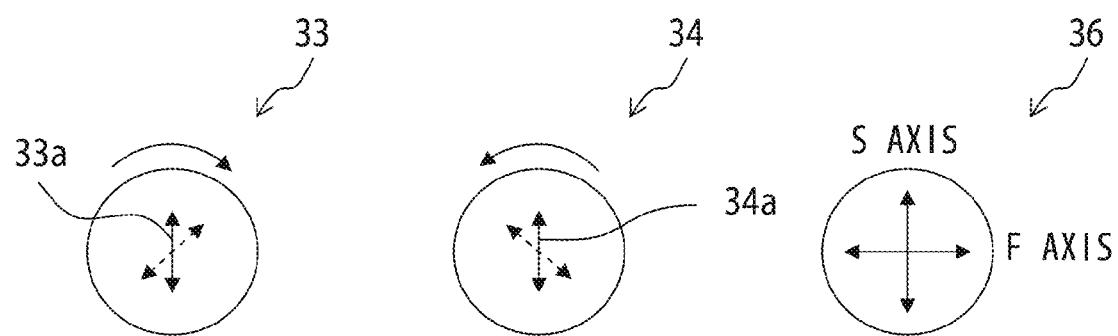
FIG. 14 is a diagram for explaining the rotation of a polarizer included in the microscope system illustrated in FIG. 13.

The polarizer 33 and the polarizer 34 are different from the polarizer 5a in FIG. 10 that they include a structure that is not illustrated in the drawing to rotate the polarizer 33 and the polaraizer 34 in tandem, and are configured to be rotated, by the structure, as illustrated in FIG. 14, with the oscillation direction 33a of the polarizer 33 and the oscillation direction 34a of the polaraizer 34 being in opposite directions in the same angle with respect to the optic axis (S axis, F axis) of the quarter wave plate 36.

Furthermore, in the polarizer 33 and the polarizer 34, a mechanism to offset the rotation angle of one of the polarizer 33 and the polarizer 34 is provided. By this mechanism, the rotation angle of one of the polarizer 33 and the polarizer 34 is offset so as to compensate for the amount of retardation generated in the half mirror of the beam splitter 35 and the like.

By the microscope system 101 configured as described above, the same effect as the microscope system 100 of Embodiment 1 can be obtained as well. Furthermore, in the microscope system 101, by making the LED light source 31 and the LED light source 32 emit the light sequentially in the state in which the polarizer 33 and the polarizer 34 are set at given symmetry rotation angles, two differential interference contrast images (I1(−θ), I1(θ)) with different contrasts in which the image of sample S is captured with settings with different amount of retardation are obtained. Meanwhile, for the light emission control of the LED light sources, it is possible to switch at a higher speed than the rotation control of polarizer 5a in the microscope system 100 of Embodiment 1, and therefore, according to the microscope system 101 according to this Embodiment, the two differential interference contrast images (I1(−θ), I1(θ)) can be obtained quickly. Therefore, it becomes possible to measure the phase distribution a higher speed than the microscope system 100 of Embodiment 1.

Meanwhile, in the microscope system 101 of this embodiment, unlike the microscope system 100 of embodiment 1, without obtaining differential interference contrast image I1(0), only the differential interference contrast images (I1(−θ), I1(θ)) are obtained. While in the phase measurement method described above, the differential interference contrast image I1(0) is also used, but the differential interference contrast image I1(0) is used to compensate for the error generated in a substance with a large phase amount, and the phase measurement may still be measured from two differential interference contrast images (I1(−θ), I1(θ)) only.

Embodiment 3

A microscope system 102 illustrated in FIG. 15 is a microscope system including a microscope 1b being a laser-scanning type differential interference contrast microscope, and is a phase measurement apparatus that executes the phase measurement method described above in the same manner as the microscope system of Embodiment 1 and Embodiment 2.

The microscope system 102 differs from the microscope system 100 of Embodiment 1 in including the microscope 1b instead of the microscope 1, and a drive mechanism 27 instead of the drive mechanism 24. Furthermore, the microscope 1b differs from the microscope 1 of Embodiment 1 in including a detecting unit 40 instead of the light source 2, the field stop 4 and the image contrast changing unit 5, and an illuminating unit 50 instead of the analyzer 11, the tube lens 12 and the CCD camera 13. That is, the microscope 1b is configured to project laser light on the biological sample S from below the stage 8, and to detect the laser light that has passed through the biological sample S.

The illuminating unit 50 includes a polarized laser light source 51, a beam scanning apparatus 52, a relay lens 53, and a mirror 54. The laser light source 51 can be a laser emitting a visible range laser light, and can also be a laser that emits near-infrared range laser for which the wavelength is longer than the visible light and scattering does not easily occur. When the sample S is thick, a laser that emits near-infrared range laser light with a wavelength of 800 nm or more is desirable. The beam scanning apparatus 52 is an apparatus for scanning the sample S with the laser light emitted from the laser light source 51, and includes a galvano mirror and the like that makes the laser light deflected at the pupil conjugate position of the objective lens 9, for example.

The detecting unit 40 is a differential detecting unit including photomultiplier tubes (PMT 41, PMT 42) being two photodetectors, and a phase modulating unit 30. The phase modulating unit 30 has the same configuration as the phase modulating unit 30 in the microscope 1a of Embodiment 2, and specifically, includes two polarizers (polarizer 33, polarizer 34) that are rotatably with respect to the optical axis, the beam splitter 35 having a half mirror, and a quarter wave plate 36 placed with its optic axis facing a certain direction. Meanwhile, here, the beam splitter 35 functions as a light separator that splits the laser light from the sample S into two and guide it to the PMT 41 and the PMT 42.

In a normal differential detecting unit, there is a limitation in the setting of retardation since the light is separated by a polarization beam splitter (PBS). By contrast, the differential detecting unit (detecting unit 40) of the microscope system 102 is different from the normal differential detecting unit in including, in order to enable the setting of the retardation according to the sample, the polarizer 33 and the polarizer 34 configured to be rotated in opposite directions with oscillation directions (oscillation direction 33a, oscillation direction 34a) being in opposite directions in the same angle with respect to the optic axis (S axis, F axis) of the quarter wave plate 36.

By the microscope system 102 configured as described above, the same effect as the microscope system 100 of Embodiment 1 may be obtained as well. Furthermore, in the microscope system 102, as the light source, the laser light source 51 that emits highly monochromatic laser light with a narrow bandwidth is used, and therefore, a differential interference contrast image with a large S/N and a high contrast can be obtained. In addition, the narrow bandwidth of the laser light also contributes to a higher accuracy of the deconvolution process. For this reason, a more accurate phase distribution can be calculated from the differential interference contrast image. Therefore, according to the microscope system 102, a more accurate phase distribution may be calculated than the microscope system 100 of Embodiment 1.

Meanwhile, when the laser light source is adopted as the light source in a normal microscope (wide-field type microscope), undesirable phenomena such as a decrease in resolution and generation of a speckle occur due to coherent illumination, but in a scanning type microscope like the microscope system 102, these phenomena do not occur. Therefore, the scanning type microscope is preferable for the use of laser light.

Meanwhile, with the scanning type microscope, compared with the wide-field type microscope, it takes time to obtain an image, and the time required to calculate the phase distribution also tends to be long. In this regard, in the microscope system 102, the calculation of the phase distribution is made faster by obtaining a plurality of images with different image contrasts simultaneously using a differential detecting unit (detecting unit 40). Specifically, the laser light emitted from the laser light source 51 and entered the differential detecting unit (detecting unit 40) is separated by beam splitter 35 into laser light going to the PMT 41 and laser light going to PMT 42, and after that, enters the PMT 41, the PMT 42 through the polarizer 33, the polarizer 34 set to symmetry rotation angles, respectively. Accordingly, in the microscope system 102, two differential interference contrast images (I1(−θ),I1(θ)) with different image contrasts in which the image of the sample S is obtained with settings with different amount of retardation may be obtained simultaneously.

Figure 16:
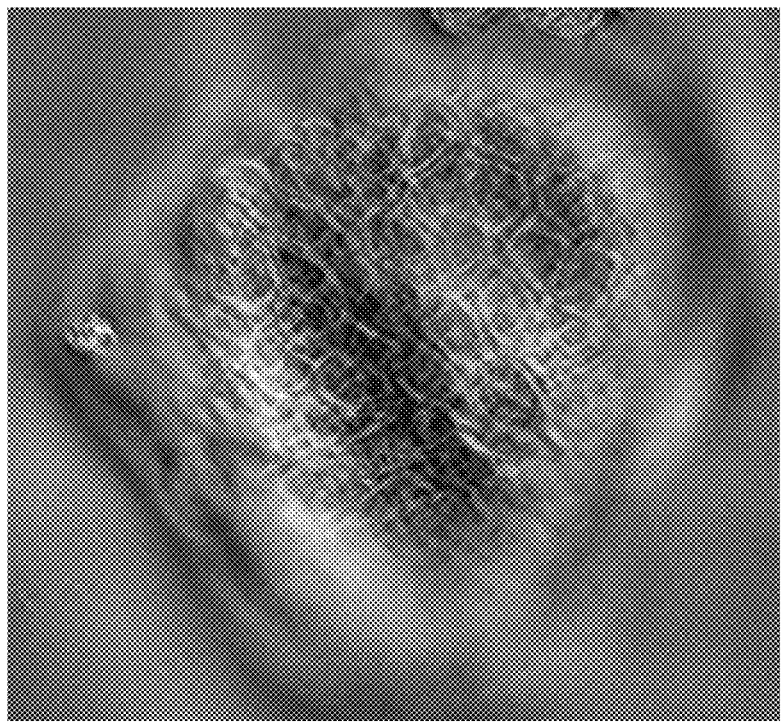
FIG. 16 is a diagram illustrating the phase distribution of a crypt in the small intestine obtained by the microscope system illustrated in FIG. 15.

FIG. 16 is a diagram illustrating the phase distribution of a crypt in the small intestine obtained by the microscope system 102. The image of the crypt in the small intestine illustrated in FIG. 16 represents the three-dimensional structure of the crypt well. Therefore, according to FIG. 16, it is confirmed that, by using the microscope system 102, it is possible to observe the three-dimensional structure of living tissues, and for example, when a mutated cell exists in the tissue, the mutated cell can be identified and observed without labeling.

Meanwhile, for the image of the crypt, an argon laser with a wavelength of 488 nm is used. Since laser is highly monochromatic, it becomes possible to perform observation with a high image contrast.

The embodiments described above illustrate specific embodiments of the present invention to facilitate understanding of the invention, and the present invention is not limited to these embodiments. For example, in the embodiments described above, a microscope system including a differential interference contrast microscope is used, but the microscope included in the microscope system is not necessarily limited to the differential interference contrast microscope, and any microscope that converts image intensity distribution into phase distribution will do. Japanese Laid-open Patent Publication No. 7-225341 discloses a technique to change the image contrast by changing the phase amount of the phase membrane of a phase-contrast microscope and to forma normalized phase component image. By adopting this technique, even in a microscope system including a phase-contrast microscope, it becomes possible to obtain the same effect as the microscope system 100.

Meanwhile, as described in the embodiments described above, the microscope system being the phase distribution measurement apparatus may be a wide-field type microscope system or may be a scanning type microscope system. In addition, any light source may be used as the light source, and any of the coherent illumination and incoherent illumination may be adopted for the microscope system.

Meanwhile, in the embodiments described above, embodiments in which the microscope system being a phase distribution measurement apparatus executes the method illustrated in FIG. 1 and FIG. 2, but the method illustrated in FIG. 8 may also be executed. In addition, Japanese Laid-open Patent Publication No. 2012-73591 discloses a microscope using oblique illumination, which makes it possible to change the image contrast by changing the direction of illumination. The same effect may be obtained using this as well.

Meanwhile, in the embodiments described above, the microscope system is described as a phase distribution measurement apparatus, but it may also be configured as an observation apparatus including a distinguishing processing unit that distinguishes the normal cell and mutated cell by image processing, using the calculated phase distribution of the biological sample. In this case, the observation apparatus may identify and display the mutated cell from another cell, when displaying the refraction index distribution for each part and the phase distribution image of the biological sample. In addition, in the distinguishing processing unit, for example, the mutated cell may be distinguished based on the cell shape (such as a different shape from other cells), size (such as the existence of a protruding part in the outline of the cell), brightness (brighter or darker than other cells, and the like), and the like.

The phase distribution measurement method, the phase distribution measurement apparatus of the prevent invention may be modified and changed in various ways within the range that does not deviate from the idea of the present invention. As is apparent from the images illustrated in FIG. 12A through FIG. 12C, and FIG. 16, according to the present invention, the structure and mutated cells in living tissues may be identified by observing the three-dimensional structure of a given biological sample without dyeing from the cell level to the tissue level (including iPS cells, ES cells, or tissues formed by differentiation of a stem cell), without dyeing the sample like in the fluorescent observation. That is, the inspection of mutation and alteration in each stage of the cell may be performed without dyeing.

What is claimed is:

1. A phase distribution measurement method a for biological sample, comprising:
    taking in an optical image of a biological sample formed by a microscope that converts phase distribution into image intensity distribution while changing image contrast to form a plurality of pieces of images with different image contrasts;
    calculating a component corresponding to phase distribution of the biological sample and a component corresponding to other than the phase distribution of the biological sample based on the plurality of pieces of images, and dividing the component corresponding to the phase distribution by the component corresponding to other than the phase distribution of the biological sample to form a normalized phase component image;
    breaking down the normalized phase component image into a plurality of frequency components based on a spatial frequency of the normalized phase component image;
    performing a deconvolution process to each of the frequency components using an optical response character corresponding to each, and calculating phase distribution of a refraction component formed by light refracted inside the biological sample and phase distribution of a structure component formed by light diffracted in a structure inside the biological sample; and
    calculating phase distribution of the biological sample by compounding the phase distribution of the refraction component and the phase distribution of the structure component.

2. The phase distribution measurement method according to claim 1, wherein:
    the breaking down of the normalized phase component image into a plurality of frequency components comprises performing an averaging process of an image to the normalized phase component image with filters having different kernel sizes, to break down the normalized phase component image, by the spatial frequency of the normalized phase component image, into a background component with a lowest spatial frequency, the refraction component, and the structure component with a highest spatial frequency.

3. The phase distribution measurement method according to claim 1, wherein:
    the microscope is a differential interference contrast microscope that performs image capturing with phase distribution of an observed object as image intensity distribution, and
    the method further comprises:
    switching a shear direction of the microscope; and
    compounding two phase distributions of the biological sample calculated in two shear directions before and after switching.

4. The phase distribution measurement method according to claim 3, further comprising:
    calculating a position misalignment amount generated when switching the shear direction from correlation of the two phase distributions of the structure component calculated in the two shear directions; and
    correcting position misalignment of the two phase distributions of the biological sample calculated in the two shear directions before and after switching using the calculated position misalignment amount.

5. The phase distribution measurement method according to claim 1, further comprising:
    performing a deconvolution process to the structure component using an optical response character in a defocus state with respect to an observation plane to calculate a second phase distribution of the structure component;
    comparing the second phase distribution of the structure component and phase distribution of the structure component calculated using an optical response character in a focused state with respect to the observation plane; and
    removing phase distribution in which blurring has occurred due to the defocus from phase distribution of the structure component based on a comparison result of phase distributions,
    wherein the calculating of phase distribution of the biological sample by compounding the phase distribution of the refraction component and the phase distribution of the structure component comprises compounding phase distribution from which the phase distribution in which blurring has occurred due to the defocus from phase distribution of the structure component is removed, and the phase distribution of the refraction component.

6. The phase distribution measurement method according to claim 5, wherein the calculating of a second phase distribution of the structure component comprises performing a deconvolution process to the structure component using an optical response character calculated in view of a phase transfer function generated due to the defocus.

7. The phase distribution measurement method according to claim 5, wherein the removing of phase distribution in which blurring has occurred due to the defocus from phase distribution of the structure component comprises forming a subtraction image by subtracting the phase distribution calculated using an optical response character in the defocus state from the phase distribution of the structure component, to separate phase distribution of the structure component within a certain depth of focus from the observation plane.

8. The phase distribution measurement method according to claim 5, wherein the removing of phase distribution in which blurring has occurred due to the defocus from phase distribution of the structure component comprises:
extracting a phase distribution in part out of a depth of focus of the microscope from the second phase distribution of the structure component, and performing convolution of the extracted phase distribution by the optical response character in the defocus state to calculate phase distribution in which blurring has occurred; and
subtracting the calculated phase distribution in which blurring has occurred from the phase distribution of the structure component.

9. The phase distribution measurement method according to claim 1, further comprising:
changing a focal plane with respect to an observation plane in an optical axis direction;
comparing phase distributions of the structure component calculated at respective focal planes to identify phase distribution leaking into the observation plane from a structure of the biological sample existing above and below the observation plane; and
removing the identified phase distribution from the phase distribution of the structure component.

10. The phase distribution measurement method according to claim 9, wherein comparing of the phase distributions comprises:
at respective focal planes, extracting an area in an XY plane that is orthogonal to an optical axis in which a phase amount of the structure component at the focal plane becomes larger than a phase amount of the structure component at adjacent focal planes above and below the focal plane; and
performing a convolution process to the phase distribution of the structure component in the extracted area, using an optical response character calculated in view of a phase transfer function generated by defocus with the adjacent focal planes above and below the focal plane.

11. The phase distribution measurement method according to claim 1, further comprising:
changing a focal plane with respect to an observation plane in an optical axis direction;
comparing phase distributions of the structure component calculated at respective focal planes to identify phase distributions of a structure of the biological sample existing continuously from front and back of the observation plane to the observation plane; and
connecting the identified phase distributions of the structure continuously.

12. A phase distribution measurement apparatus comprising:
a microscope configured to convert phase distribution of a biological sample into image intensity distribution, comprising an image contrast changing unit configured to change image contrast of the image intensity distribution;
a control unit configured to control the image contrast changing unit so as to obtain a plurality of pieces of images with different image contrasts; and
a calculating unit configured to calculate phase distribution of the biological sample from the plurality of pieces of images obtained by control the control unit performs,
wherein the calculating unit is configured to:
take in an optical image of the biological sample formed by the microscope while changing image contrast to form the plurality of pieces of images with different image contrasts,
calculate a component corresponding to phase distribution of the biological sample and a component corresponding to other than the phase distribution of the biological sample based on the plurality of pieces of images, and divide the component corresponding to the phase distribution by the component corresponding to other than the phase distribution of the biological sample to form a normalized phase component image,
break down the normalized phase component image into a plurality of frequency components based on a spatial frequency of the normalized phase component image,
perform a deconvolution process to each of the frequency components using an optical response character corresponding to each, and calculate phase distribution of a refraction component formed by light refracted inside the biological sample and phase distribution of a structure component formed by light diffracted in a structure inside the biological sample, and
calculate phase distribution of the biological sample by compounding the phase distribution of the refraction component and the phase distribution of the structure component.

13. The phase distribution measurement apparatus according to claim 12, wherein the phase distribution measurement apparatus is configured to measure an inside structure of an cultured ES cell or iPS cell being the biological sample.

14. The phase distribution measurement apparatus according to claim 13, wherein the phase distribution measurement apparatus is configured to distinguish a normal cell and a mutated cell inside a colony of the ES cell or the iPS cell.

15. The phase distribution measurement apparatus according to claim 13, wherein the phase distribution measurement apparatus is configured to identify an undifferentiated state of the ES cell or the iPS cell.

16. The phase distribution measurement apparatus according to claim 12, wherein the phase distribution measurement apparatus is configured to identify a mutated cell inside a tissue formed by differentiation of an ES cell or an iPS cell.

17. The phase distribution measurement apparatus according to claim 12, wherein the phase distribution measurement apparatus is configured to identify a structure in a tissue and a mutated cell formed by differentiation of a stem cell.

18. The phase distribution measurement apparatus according to claim 12, wherein the phase distribution measurement apparatus is configured to identify a mutated cell in a living tissue without labeling.

19. A phase distribution measurement apparatus comprising:
a microscope configured to convert phase distribution of a biological sample into image intensity distribution, comprising an image contrast changing unit configured to change image contrast of the image intensity distribution;
a control unit configured to control the image contrast changing unit so as to obtain a plurality of pieces of images with different image contrasts; and
a calculating unit configured to calculate phase distribution of the biological sample from the plurality of pieces of images obtained by control the control unit performs, wherein the calculating unit is configured to:
    take in an optical image of the biological sample formed by the microscope while changing image contrast to form the plurality of pieces of images with different image contrasts,
    calculate a component corresponding to phase distribution of the biological sample and a component corresponding to other than the phase distribution of the biological sample based on the plurality of pieces of images, and divide the component corresponding to the phase distribution by the component corresponding to other than the phase distribution of the biological sample to form a normalized phase component image,
    break down the normalized phase component image into a plurality of frequency components based on a spatial frequency of the normalized phase component image,
    perform a deconvolution process to each of the frequency components using an optical response character corresponding to each, and calculate phase distribution of a refraction component formed by light refracted inside the biological sample and phase distribution of a structure component formed by light diffracted in a structure inside the biological sample,
    perform a deconvolution process to the structure component using an optical response character in a defocus state with respect to an observation plane to calculate a second phase distribution of the structure component,
    compare the second phase distribution of the structure component and phase distribution of the structure component calculated using an optical response character in a focused state with respect to the observation plane,
    remove phase distribution in which blurring has occurred due to the defocus from phase distribution of the structure component based on a comparison result of phase distributions, and
    calculate phase distribution of the biological sample by compounding the phase distribution of the refraction component and the phase distribution of the structure component,
wherein the calculating of phase distribution of the biological sample by compounding the phase distribution of the refraction component and the phase distribution of the structure component comprises compounding phase distribution from which the phase distribution in which blurring has occurred due to the defocus from phase distribution of the structure component is removed, and the phase distribution of the refraction component.

20. A phase distribution measurement apparatus comprising:
    a microscope configured to convert phase distribution of a biological sample into image intensity distribution, comprising an image contrast changing unit configured to change image contrast of the image intensity distribution;
    a focus position control unit configured to change a focal plane with respect to an observation plane in an optical axis direction;
    a control unit configured to control the image contrast changing unit so as to obtain a plurality of pieces of images with different image contrasts; and
    a calculating unit configure to calculate phase distribution of the biological sample from which phase distribution leaking from a structure of the biological sample existing above and below the observation plane is removed, from the plurality of pieces of images obtained by control the control unit performs,
wherein the calculating unit is configured to:
    take in an optical image of the biological sample formed by the microscope while changing image contrast to form the plurality of pieces of images with different image contrasts,
    calculate a component corresponding to phase distribution of the biological sample and a component corresponding to other than the phase distribution of the biological sample based on the plurality of pieces of images, and divide the component corresponding to the phase distribution by the component corresponding to other than the phase distribution of the biological sample to form a normalized phase component image,
    break down the normalized phase component image into a plurality of frequency components based on a spatial frequency of the normalized phase component image,
    perform a deconvolution process to each of the frequency components using an optical response character corresponding to each, and calculate phase distribution of a refraction component formed by light refracted inside the biological sample and phase distribution of a structure component formed by light diffracted in a structure inside the biological sample,
    change a focal plane with respect to an observation plane in an optical axis direction,
    compare phase distribution of the structure component calculated at respective focal planes to identify phase distribution leaking into the observation plane from a structure of the biological sample existing above and below the observation plane,
    remove the identified phase distribution from the phase distribution of the structure component, and
    calculate phase distribution of the biological sample by compounding the phase distribution of the refraction component and the phase distribution of the structure component.

* * * * *